United States Patent
Hagihara et al.

[11] Patent Number: 6,096,692
[45] Date of Patent: Aug. 1, 2000

[54] SYNTHETIC LUBRICATING OIL

[75] Inventors: Toshiya Hagihara, Izumisano; Shoji Nakagawa, Wakayama; Yuichiro Kobayashi, Wakayama; Hiroyasu Togashi, Wakayama; Koji Taira, Wakayama; Akimitsu Sakai, Wakayama, all of Japan

[73] Assignee: Kao Corporation, Tokyo, Japan

[21] Appl. No.: 08/776,751

[22] PCT Filed: Feb. 27, 1995

[86] PCT No.: PCT/JP95/00304

§ 371 Date: Feb. 13, 1996

§ 102(e) Date: Feb. 13, 1996

[87] PCT Pub. No.: WO96/06839

PCT Pub. Date: Mar. 7, 1996

[30] Foreign Application Priority Data

Aug. 29, 1994 [JP] Japan ................................. 6-228616
Oct. 31, 1994 [JP] Japan ................................. 6-292431

[51] Int. Cl.$^7$ ..................... C10M 105/18; C07D 317/18
[52] U.S. Cl. .............................. 508/307; 549/372; 252/68
[58] Field of Search .................... 508/307; 252/67, 252/68; 549/372

[56] References Cited

U.S. PATENT DOCUMENTS

| | | | |
|---|---|---|---|
| 1,934,309 | 11/1933 | Hoover | 549/372 |
| 3,714,202 | 1/1973 | Nakaguchi et al. | 549/372 |
| 3,725,438 | 4/1973 | Barone et al. | 549/372 |
| 3,741,986 | 6/1973 | Hartmann | 549/372 |
| 3,900,411 | 8/1975 | Andress, Jr. | 508/307 |
| 3,910,845 | 10/1975 | Coon | 508/307 |
| 4,076,727 | 2/1978 | Zey et al. | 252/68 |
| 4,659,809 | 4/1987 | Matsumura . | |
| 4,755,316 | 7/1988 | Magid et al. . | |
| 4,851,144 | 7/1989 | McGraw et al. . | |
| 5,395,544 | 3/1995 | Hagihara et al. | 252/68 |
| 5,523,010 | 6/1996 | Sorensen et al. | 508/307 |
| 5,575,944 | 11/1996 | Sawada et al. . | |
| 5,720,895 | 2/1998 | Nakagawa et al. | 252/68 |

FOREIGN PATENT DOCUMENTS

| | | |
|---|---|---|
| 0696564 | 2/1996 | European Pat. Off. . |
| 2003067 | 8/1970 | Germany . |
| 59-25892 | 2/1984 | Japan . |
| 4320498 | 11/1992 | Japan . |
| 657243 | 3/1994 | Japan . |

OTHER PUBLICATIONS

Chemical Abstracts, vol. 77, No. 9, Abstract No. 61237u (XP–002097541), Jun. 29, 1990.

*Primary Examiner*—Jacqueline V. Howard
*Attorney, Agent, or Firm*—Birch, Stewart, Kolasch & Birch, LLP

[57] ABSTRACT

The present invention relates to a synthetic lubricating oil comprising cyclic ketals or cyclic acetals obtained by a reaction between one or more polyhydric alcohols having an even number of hydroxyl groups of not less than 4 and not more than 10 and one or more specific carbonyl compounds, or one or more ketals or acetals which are reactive derivatives of said carbonyl compounds; a working fluid composition for a refrigerating machine comprising a hydrofluorocarbon and a refrigeration oil containing the cyclic ketals or cyclic acetals; and novel compounds of the above cyclic acetals and a production method thereof. The present invention provides a synthetic lubricating oil which shows a good thermal stability, a good oxidation resistance, no carboxylic acid formation due to hydrolysis and a low hygroscopicity and is inexpensive as well. Also, a working fluid composition for a refrigerating machine which shows a good insulating property, favorable hygroscopicity, and no carboxylic acid formation due to hydrolysis as well as being inexpensive can be provided.

7 Claims, No Drawings

SYNTHETIC LUBRICATING OIL

This application is a 371 of PCT/JP95/00304 filed Feb. 27, 1995.

TECHNICAL FIELD

The present invention relates to a synthetic lubricating oil using, as a base oil, cyclic ketals or cyclic acetals having a particular structure, and also to a working fluid composition for a refrigerating machine which uses the synthetic lubricating oil.

The present invention further relates to cyclic acetals which are useful as polar oils, organic solvents, lubricants, synthetic lubricating oils, or refrigeration oils, or as intermediates in the production of surfactants, organic solvents, polar oils, synthetic lubricating oils, refrigeration oils, etc., and to a method for producing the cyclic acetals.

BACKGROUND ART

With lengthened intervals of oil changes, need of energy-saving, use of high performance machines, and down-sizing of machines, demand for the performance of lubricating oils has become severe. In particular, lubricating oils with a high thermal stability and a high oxidation resistivity have been strongly sought. In the situation where there has been increasing public concern about global environmental pollution, such as depletion of ozone layer caused by freon, the earth warming due to excess carbon dioxide and methane, destruction of forests by sulfur dioxide and $NO_x$ in exhaust fumes, and pollution of soil and lakes due to chemical leakage, environmental protective measures have been strongly sought also in the field of lubricating oils.

In order to meet the requirements for high thermal stability and oxidation resistivity, ethers, such as polyalkylene glycols, and esters, such as aliphatic diesters and hindered esters, have been developed and used for engine oils, hydraulic oils, grease base oils, gear oils, rolling oils, precision instrument oils, etc.

However, ethers, such as polyalkylene glycols, have a higher polarity than conventionally used mineral oils to cause the following drawbacks: (1) high hygroscopicity, and (2) insolubility of additives which are conventionally used for lubricating oils. An ether synthesized from an alkyl halide and a polyol, which has a lower polarity than polyalkylene glycols, is described in Japanese Patent Examined Publication No. 1-29240. This ether also has a problem that a trace of residual halogen in the ether product may impair thermal stability and oxidation resistivity.

Esters also are not free from drawbacks. That is, carboxylic acid formed by hydrolysis of esters erodes metals, and esters tend to impair the effects of oiliness improvers and extreme pressure additives, though esters have a merit to reduce friction because they are well adsorbed onto metals.

Thus, synthetic lubricating oils with adequately low polarity, high thermal stability, high oxidation resistivity, no formation of carboxylic acids due to hydrolysis and low hygroscopicity are in high demand.

Recently, the use of dichlorodifluoromethane (CFC12) for refrigerators and car air conditioners is restricted, and will be legally banned at the end of 1995 in order to protect the ozone layer from the viewpoint of the environment of the earth, and also the use of chlorodifluoromethane (HCFC22) for room air conditioners is about to be legally regulated. Thus, hydrofluorocarbons which do not destroy the ozone layer, such as 1,1,1,2-tetrafluoroethane (HFC 134a), difluoromethane (HFC32), and pentafluoroethane (HFC125), have been developed as substitutes for CFC12 or HCFC22.

However, since the polarity of hydrofluorocarbons is higher than that of CFC12 or HCFC22, the use of conventional lubricating oils, such as naphthene mineral oils, poly-α-olefins and alkylbenzenes, causes two-phase separation of the working fluid at low temperatures. This is due to poor compatibility between the conventional lubricating oils and the hydrofluorocarbons. Two-phase separation hampers oil return, which in turn interferes with heat transfer due to deposition of a thick oil film around the condenser and evaporator used as heat exchangers. It can also cause significant failures, such as poor lubrication and foaming upon starting operation. Therefore, the conventional refrigeration oils cannot be used as refrigeration oils under these new refrigerant atmospheres. With this being the situation, lubricating oils with good compatibility with hydrofluorocarbons have been sought.

As for lubricity, CFC12 and HCFC22 generate hydrogen chloride upon its partial decomposition. The hydrogen chloride thus formed reacts with the friction surface to form a coating of chlorides, thereby improving the lubricity. On the other hand, hydrofluorocarbons containing no chlorine atoms are not expected to have such an effect; therefore, the refrigeration oils used in combination with hydrofluorocarbons are required to have a further excellent lubricity when compared to the conventional refrigeration oils.

In addition, the refrigeration oils used in combination with hydrofluorocarbons have to have good thermal stability in the presence of hydrofluorocarbons.

Moreover, in the compression-type refrigerating machines for electric refrigerators and air conditioners, since organic materials are used for motor components such as insulators and enameled wires, the working fluid comprising a hydrofluorocarbon and a refrigeration oil is required to have no adverse effects on the organic materials and also have a good insulating property.

As refrigeration oils which can be used in combination with hydrofluorocarbons such as 1,1,1,2-tetrafluoroethane (HFC134a), polyalkylene glycol compounds are disclosed in U.S. Pat. No. 4,755,316 (Japanese Patent Unexamined Application No. 2-502385), Japanese Patent Laid-Open No. 3-14894 (European Patent No. 377122), and Japanese Patent Laid-Open No. 2-182780 (WO90/05172).

Since polyalkylene glycol compounds have a higher polarity than naphthene mineral oils, their compatibility with HFC134a at low temperatures is certainly good. However, polyalkylene glycol compounds have a problem to cause phase separation as the temperature increases, as mentioned in U.S. Pat. No. 4,755,316. There are also several other problems about polyalkylene glycol compounds. A poor insulating property is one of the problems. Due to this significant problem, polyalkylene glycol compounds cannot be used for refrigerating devices of electric refrigerators and air conditioners where a motor is incorporated in a compressor. Therefore, applications of polyalkylene glycol compounds are proposed for car air conditioners where their poor insulating property does not cause any problems. High hygroscopicity is another significant problem of polyalkylene glycol compounds. Water absorbed by the compounds causes thermal instability in the presence of HFC134a and hydrolysis of organic materials such as PET films. Insulating property can be improved and hygroscopicity is decreased by reducing the number of ether bonds per unit weight of polyalkylene glycol compounds, but the compatibility with hydrofluorocarbons becomes poor. Thus, ether compounds like polyalkylene glycol compounds cannot have both good compatibility with hydrofluorocarbons and good insulating property/decreased hygroscopicity at the same time.

In order to solve the above problems of polyalkylene glycol compounds, such as poor insulating property and high hygroscopicity, ester compounds and carbonate compounds have been developed. For example, the following compounds are disclosed as refrigeration oils which can be used in combination with 1,1,1,2-tetrafluoroethane (HFC134a): mixed oils of polyalkylene glycol compounds and ester oils are disclosed in U.S. Pat. No. 4,851,144 (corresponding to Japanese Patent Laid-Open No. 2-276894) and Japanese Patent Laid-Open No. 2-158693; ester oils are disclosed in Japanese Patent Unexamined Application No. 3-505602 (WO90/12849) and Japanese Patent Laid-Open Nos. 3-128991, 3-128992, 3-88892, and 3-179091; and carbonate oils are disclosed in Japanese Patent Laid-Open Nos. 2-132178 and 3-149295, and European Patent No. 421,298.

Ester compounds and carbonate compounds show good compatibility with hydrofluorocarbons and high thermal stability in the presence of hydrofluorocarbons. Also, these compounds have markedly better insulating properties and much lower hygroscopicity than polyalkylene glycol compounds. However, compared with the conventional CFC12-mineral oil working fluid system, both freon and oil tend to have a high polarity in the hydrofluorocarbon-ester oil system or hydrofluorocarbon-carbonate oil system, and the systems become highly hygroscopic. Therefore, esters tend to be hydrolyzed to form carboxylic acids, and the formed carboxylic acids may in turn erode metals and cause to wear down the metals. Also, in the case of using a carbonate oil, there arises a problem that a non-condensable carbon dioxide gas is generated owing to hydrolysis of the carbonate oil to cause low refrigerating capacity.

In particular, in the case of room air conditioners, it is common practice to fill an air conditioner with a refrigerant upon installation. Therefore, unlike refrigerating machines for which filling of refrigerant is carried out in a factory, it is almost impossible to prevent a working fluid of room air conditioners from being contaminated with water. Therefore, there has been a concern about the reliability of the hydrofluorocarbon-ester oil system and hydrofluorocarbon-carbonate oil system, when these systems are used in room air conditioners.

WO93/24435 discloses a polyvinyl ether compound as a polyether compound which is free from the problem of poor insulating property of polyalkylene glycols. This polyvinyl ether compound is prepared by polymerization of vinyl ether monomers and subsequent hydrogenation. It is described that the compound has a good compatibility with hydrofluorocarbons and good insulating property. However, since the polyvinyl ether compound is synthesized by polymerization, it shows molecular weight distribution. Therefore, a part of high molecular weight polymers sometimes causes plugged capillaries and worsens the compatibility of the compound with hydrofluorocarbon. Also, the compound requires complicated post-treatment and cannot always be obtained in a high yield because vinyl ether monomers, the starting materials of the polyvinyl ether compound, are not stable substances. In particular, the yield of those with low degree of polymerization (around 6) is low. Some vinyl ether monomers of certain structures cannot be easily obtained, and are, therefore, very expensive.

Alternatively, Japanese Patent Laid-Open Nos. 4-320498 and 6-57243 disclose the use of cyclic ketals and cyclic acetals for a working fluid composition for a refrigerating machine. In the former publication, it is disclosed that ketals or acetals prepared from monohydric or dihydric alcohols and ketones or aldehydes are used in combination with a synthetic lubricating oil of ester or polyalkylene glycol type. In the latter publication, ester or carbonate derivatives of glycerol, trimethylolethane, trimethylolpropane and pentaerythritol, which have ketal or acetal groups in the molecules, are disclosed. The acetals and ketals disclosed in the former publication have drawbacks of small molecular weight and low boiling and flashing points. The acetals and ketals disclosed in the latter publication have drawbacks of high cost because their production has two or more reaction steps. Some acetals or ketals in the latter publication also have a drawback of difficulty in producing them at high purity. Also, acetals and ketals disclosed in the latter publication have 2 or more ether bonds in a molecule, resulting in unsatisfactory improvement of insulating property.

The refrigerant-oil systems developed so far have some problems as mentioned above. The hydrofluorocarbon-polyalkylene glycol oil system has problems in hygroscopicity and insulating property; and the hydrofluorocarbon-ester oil system and the hydrofluorocarbon-carbonate oil system have problems of poor resistance against hydrolysis. Both of these systems are unsatisfactory as a working fluid composition for a refrigerating machine, because they have higher hygroscopicity as compared with the conventional CFC12-mineral oil system and cause thermal instability, deterioration of organic materials, and corrosion and wear of metals. Polyvinyl ether compounds show a molecular weight distribution, and therefore partially contain molecules with high molecular weights, which cause to lower the compatibility with hydrofluorocarbons. Polyvinyl ether compounds also have drawbacks of limited availability of the starting materials and high cost. Ketals and acetals reported so far have drawbacks of low molecular weight and high cost.

It is common practice to form cyclic acetals by using acetone as a ketone for the purpose of protection in the field of sugar and polyol synthesis. Recently, 1,3-dioxolan synthesized from formaldehyde and ethylene glycol is on the market as an organic solvent.

As for cyclic acetals formed from sorbitol and benzaldehyde, dibenzylidenesorbitol is known as a gelling agent. Also, cyclic acetals for med from an unsaturated aldehyde and sorbitol are utilized as a starting material of polymers.

Also, cyclic acetals formed between sorbitol and acetone, formaldehyde, acetaldehyde, or butyraldehyde are known. However, cyclic acetals having longer, linear or branched chains have not yet been known. Cyclic acetals formed between sorbitol and isobutyraldehyde are not known.

Cyclic acetals are used as organic solvents as mentioned above, as solvents for ink and paint, as additives or gelling agents, as starting materials for polymers, as absorbents for absorption refrigerating machines (Japanese Patent Laid-Open No. 59-25892), or as dehydrating agents for refrigeration oils (Japanese Patent Laid-Open Nos. 4-320498 and 6-57243).

Cyclic ketals have been formed between hexahydric alcohols, such as sorbitol and mannitol, and acetone for the purposes of protection of a compound and identification of structures. However, such cyclic ketals have high melting points and can hardly be used as polar oils, synthetic lubricating oils and refrigeration oils which are required to be in a liquid state around room temperature. Although cyclic ketals having unsaturated alkyl chains have lower melting points, they have drawbacks in stability. Those having aromatic rings such as a phenyl ring are to be gelatinized, and therefore, unsuitable as polar oils, synthetic lubricating oils, and refrigeration oils. On the other hand, cyclic acetals formed from lower hydric alcohols, such as ethylene glycol, have low viscosity and, therefore, unsuitable for the use in synthetic lubricating oils and refrigeration oils.

DISCLOSURE OF THE INVENTION

Accordingly, it is an object of the present invention to provide a synthetic lubricating oil which is excellent in thermal stability and oxidation resistivity, free from carboxylic acids formation due to hydrolysis, low in hygroscopicity, and inexpensive; and to provide an inexpensive working fluid composition for a refrigerating machine which is free from formation of carboxylic acid and has good performance with respect to compatibility with hydrofluorocarbon, insulating property, and hygroscopicity.

It is another object of the present invention to provide novel cyclic acetals suitably used for synthetic lubricating oils and refrigeration oils. It is still another object of the present invention to provide a method for producing the novel cyclic acetals in high yield by simple procedures.

As a result of intensive research in view of the above objects, the present inventors noted ether compounds as a structure which does not generate carboxylic acid or carbon dioxide and found that ketals or acetals having a certain structure have extremely high insulating properties. The inventors succeeded in obtaining a compound having good compatibility with hydrofluorocarbons and high insulating property/low hygroscopicity at the same time, which the conventional ether compounds do not have, and have completed the present invention.

In brief, the present invention is concerned with:

(1) A synthetic lubricating oil comprising cyclic ketals or cyclic acetals obtained by a reaction between one or more polyhydric alcohols having an even number of hydroxyl groups of not less than 4 and not more than 10 and one or more carbonyl compounds represented by the general formula (I):

(I)

wherein $R^1$ represents a hydrogen atom or a linear, branched, or cyclic alkyl group having 1–18 carbon atoms; $R^2$ represents a linear, branched, or cyclic alkyl group having 1–18 carbon atoms; $R^1$ and $R^2$ together may represent an alkylene group having 2–36 carbon atoms, or one or more ketals or acetals which are reactive derivatives of the carbonyl compounds;

(2) A synthetic lubricating oil comprising cyclic ketals or cyclic acetals obtained by a reaction between one or more polyhydric alcohols having an even number of hydroxyl groups of not less than 4 and not more than 8 and one or more carbonyl compounds represented by the general formula (II):

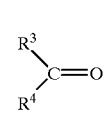

(II)

wherein $R^3$ represents a hydrogen atom or a linear, branched, or cyclic alkyl group having 1–12 carbon atoms; $R^4$ represents a linear, branched, or cyclic alkyl group having 1–12 carbon atoms; $R^3$ and $R^4$ together may represent an alkylene group having 2–13 carbon atoms, a total carbon atoms of $R^3$ and $R^4$ being 1–13, or one or more ketals or acetals, which are reactive derivatives of said carbonyl compounds.

(3) The synthetic lubricating oil as described in (1) or (2) above, wherein the polyhydric alcohols have no ether bond;

(4) The synthetic lubricating oil as described in (1) or (2) above, wherein the polyhydric alcohols have one ether bond;

(5) The synthetic lubricating oil as described in (3) or (4) above, wherein the cyclic ketals or cyclic acetals comprise a 1,3-dioxolan structure and/or a 1,3-dioxane structure;

(6) The synthetic lubricating oil as described in any one of (3) to (5) above, comprising cyclic ketals or cyclic acetals obtained by a reaction between a tetrahydric or hexahydric saturated aliphatic alcohol having 4–25 carbon atoms and one or more carbonyl compounds represented by the general formula (II), or one or more ketals or acetals which are reactive derivatives of said carbonyl compounds;

(7) A synthetic lubricating oil comprising one or more cyclic ketals or cyclic acetals represented by the general formula (IIIa), (IIIb), (IVa), or (IVb):

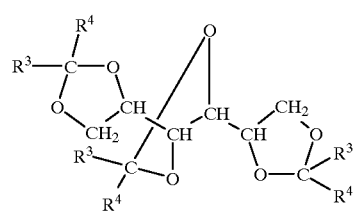

(IIIa)

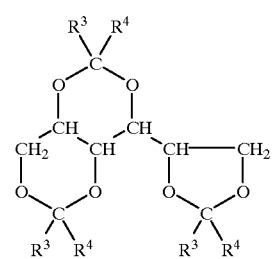

(IIIb)

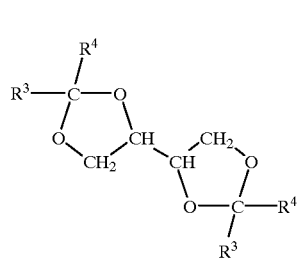

(IVa)

-continued (IVb)

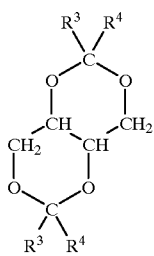

wherein $R^3$ represents a hydrogen atom or a linear, branched, or cyclic alkyl group having 1–12 carbon atoms, $R^4$ represents a linear, branched, or cyclic alkyl group having 1–12 carbon atoms, or $R^3$ or $R^4$ together may represent an alkylene group having 2–13 carbon atoms, a total carbon atoms of $R^3$ and $R^4$ being 1–13;

(8) A synthetic lubricating oil comprising one or more cyclic ketals or cyclic acetals represented by the general formula (V) or (VI):

(V)

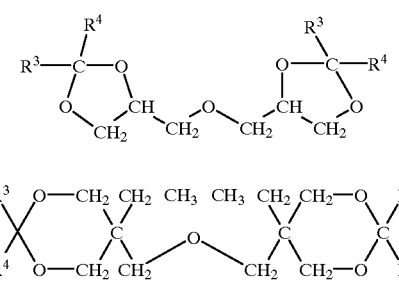

(VI)

wherein $R^3$ represents a hydrogen atom or a linear, branched, or cyclic alkyl group having 1–12 carbon atoms, $R^4$ represents a linear, branched, or cyclic alkyl group having 1–12 carbon atoms, or $R^3$ and $R^4$ together may represent an alkylene group having 2–13 carbon atoms, a total carbon atoms of $R^3$ and $R^4$ being 1–13;

(9) A working fluid composition for a refrigerating machine comprising a refrigeration oil containing the cyclic ketals or cyclic acetals described in any one of (2) to (8) above and a hydrofluorocarbon;

(10) The working fluid composition for a refrigerating machine as described in (9) above, wherein the hydrofluorocarbon and the refrigerating oil are contained at hydrofluorocarbon/refrigerating oil (weight ratio) of 50/1 to 1/20;

(11) Cyclic acetals represented by the following general formula (i) or (ii):

(i)

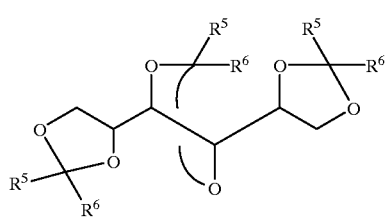

(ii)

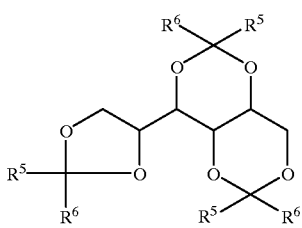

wherein $R^5$ represents a hydrogen atom and $R^6$ represents a branched alkyl group having 3 carbon atoms or a linear or branched alkyl group having 4–21 carbon atoms; or $R^5$ represents a linear or branched alkyl group having 1–21 carbon atoms, and $R^6$ represents a linear or branched alkyl group having 2–21 carbon atoms;

(12) The cyclic acetals as described in (11) above, wherein $R^5$ represents a hydrogen atom, and $R^6$ represents a branched alkyl group having 3 carbon atoms or a linear or branched alkyl group having 4–12 carbon atoms; or $R^5$ represents a linear or branched alkyl group having 1–12 carbon atoms, and $R^6$ represents a linear or branched alkyl group having 2–12 carbon atoms;

(13) The cyclic acetals as described in (11) above, wherein $R^5$ represents a hydrogen atom, and $R^6$ represents a branched alkyl group having 3–12 carbon atoms; or $R^5$ represents a linear or branched alkyl group having 1–12 carbon atoms, and $R^6$ represents a linear or branched alkyl group having 2–12 carbon atoms;

(14) The cyclic acetals as described in any one of (11) to (13) above, wherein a hexahydric alcohol residue is derived from sorbitol;

(15) A method for producing the cyclic acetal represented by the general formula (i) or (ii) as described in (11) above, comprising:

reacting hexahydric alcohols represented by the following formula (iii):

(iii)

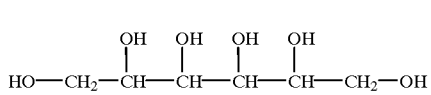

with carbonyl compounds represented by the following formula (iv):

(iv)

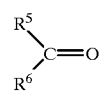

wherein $R^5$ represents a hydrogen atom, and $R^6$ represents a branched alkyl group having 3 carbon atoms or a linear or branched alkyl group having 4–21 carbon atoms; or $R^5$ represents a linear or branched alkyl group having 1–21 carbon atoms and $R^6$ represents a linear or branched alkyl group having 2–21 carbon atoms, or with a reactive derivative thereof (ketals or acetals), in the presence of an acid catalyst; and

(16) The method as described in (15) above, wherein the hexahydric alcohol is sorbitol.

BEST MODE FOR CARRYING OUT THE INVENTION

The present invention encompasses a synthetic lubricating oil and a working fluid composition for a refrigerating machine comprising specific cyclic ketals or cyclic acetals. Among the cyclic ketals or cyclic acetals, novel compounds having particular structures are also encompassed by the present invention. In the present specification, for the convenience sake, the former is referred to as the first invention and the latter as the second invention, and both the inventions are hereinafter described separately. First, the first invention is described.

Polyhydric alcohols used in the first invention are polyhydric alcohols having an even number of hydroxyl groups of not less than 4 and not more than 10. When the number of hydroxyl groups of a polyhydric alcohol is an odd number, hydroxyl groups are necessarily to remain unchanged, which undesirably makes the viscosity high. In case where the product is used for a working fluid composition for a refrigerating machine, unchanged hydroxyl groups impair compatibility with hydrofluorocarbon undesirably. Though viscosity and compatibility can be improved by alkylating the unchanged hydroxyl groups to form an ether structure, this undesirably increases the number of reaction steps in the production process. This increase in reaction step also makes it difficult to obtain the product of high purity. Specifically, examples include polyhydric alcohols such as erythritol, diglycerol, arabinose, ribose, sorbitol, mannitol, galactitol, iditol, talitol, allitol, 4,7-dioxadecane-1,2,9,10-tetrol, 5-methyl-4,7-dioxadecane-1,2,9,10-tetrol, 4,7,10-trioxatridecane-1,2,12,13-tetrol, 1,6-dimethoxyhexane-2,3,4,5-tetrol, and 3,4-diethoxyhexane-1,2,5,6-tetrol; and hindered alcohols such as pentaerythritol, ditrimethylolethane, ditrimethylolpropane, dipentaerythritol, tripentaerythritol, 2,9-diethyl-2,9-dihydroxymethyl-4,7-dioxadecane-1,10-diol, and 2,12-diethyl-2,12-dihydroxymethyl-5,8-dimethyl-4,7,10-trioxatridecane-1,13-diol. Of the above examples, polyhydric alcohols having 2 or more ether bonds, such as 4,7-dioxadecane-1,2,9,10-tetrol, 5-methyl-4,7-dioxadecane-1,2,9,10-tetrol, 4,7,10-trioxatridecane-1,2,12,13-tetrol, 1,6-dimethoxyhexane-2,3,4,5-tetrol, 3,4-diethoxyhexane-1,2,5,6-tetrol, 2,9-diethyl-2,9-dihydroxymethyl-4,7-dioxadecane-1,10-diol, and 2,12-diethyl-2,12-dihydroxymethyl-5,8-dimethyl-4,7,10-trioxatridecane-1,13-diol, are difficult to obtain on an industrial scale, and require several steps for production thereof, resulting in undesirably high cost.

The polyhydric alcohols used in the first invention have 4, 6, 8, or 10 hydroxyl groups, preferably 4, 6, or 8 hydroxyl groups, more preferably 4 or 6 hydroxyl groups. When the number of hydroxyl groups is more than 10, viscosity of the obtained cyclic ketals or cyclic acetals becomes too high. When the number is less than 4, the molecular weight becomes too low, making boiling and flashing points undesirably low.

The polyhydric alcohols used in the first invention have 4–25 carbon atoms, preferably 4–20 carbon atoms. When the number of carbon atoms is more than 25, the viscosity of the cyclic ketals or cyclic acetals obtained becomes too high. When the number of carbon atoms is less than 4, the molecular weight becomes too low, making boiling and flashing points undesirably low.

The polyhydric alcohols used in the first invention are saturated aliphatic alcohols. When there is an unsaturated bond, thermal stability becomes undesirably poor.

In view of good insulating property, it is the most preferable for the polyhydric alcohols used in the first invention not to have any ether bond in the molecule. If any, it is preferable to limit the number of ether bond to one. When there are two or more ether bonds, insulating property becomes poor, and, therefore, undesirable when used for insulating oils or working fluid compositions for a refrigerating machine. Examples of the polyhydric alcohols having no ether bond in the molecule include erythritol, sorbitol, mannitol, galactitol, iditol, talitol, allitol, and pentaerythritol; and examples of the polyhydric alcohols having one ether bond include diglycerol, ditrimethylolpropane, and ditrimethylolethane.

When the cyclic ketals or cyclic acetals in the first invention are used for a working fluid composition for a refrigerating machine, the polyhydric alcohols have preferably 4, 6, or 8 hydroxyl groups, more preferably 4 or 6 hydroxyl groups. When the number of hydroxyl groups of the polyhydric alcohols is more than 8, the viscosity becomes too high, and compatibility with hydrofluorocarbons becomes poor. When the number of hydroxyl groups is less than 4, molecular weight becomes undesirably low, thereby making the boiling and flashing points undesirably low. The number of carbon atoms is preferably 4–20, more preferably 4–15, still more preferably 4–10. When the number of carbon atoms is more than 20, compatibility with hydrofluorocarbon becomes undesirably poor. When the number of carbon atoms is less than 4, molecular weight becomes too low, thereby making boiling and flashing points undesirably low. When an alcohol with highly symmetric structure, such as pentaerythritol, is used, the cyclic ketals or cyclic acetals obtained become unsuitable for the use in a working fluid composition for a refrigerating machine because melting point becomes high.

The carbonyl compounds used in the first invention are ketones or aldehydes represented by the following general formula (I):

(I)

The number of carbon atoms of the ketones or aldehydes represented by the general formula (I) is 2–37, preferably 2–25, more preferably 2–17. When the number of carbon atoms is more than 37, viscosity of the cyclic ketals or cyclic acetals obtained becomes undesirably high.

$R^1$ is a hydrogen atom, or a linear, branched, or cyclic alkyl group having 1–18 carbons atoms, preferably a hydrogen atom, or a linear, branched, or cyclic alkyl group having 1–12 carbon atoms, more preferably a hydrogen atom, or a linear, branched or cyclic alkyl group having 1–8 carbon atoms. $R^2$ is a linear, branched, or cyclic alkyl group having 1–18 carbon atoms, preferably a linear, branched, or cyclic alkyl group having 1–12 carbon atoms, more preferably a linear, branched or cyclic alkyl group having 1–8 carbon atoms. Alternatively, $R^1$ and $R^2$ together may form an alkylene group having 2–36 carbon atoms, preferably 2–24 carbon atoms, more preferably 2–16 carbon atoms. $R^1$ and $R^2$ may or may not be identical.

When the number of carbon atoms of $R^1$ or $R^2$ is more than 18, viscosity of the cyclic ketals or cyclic acetals obtained becomes undesirably high. When the number of carbon atoms of the alkylene group which $R^1$ and $R^2$ together form is more than 36, viscosity of the cyclic ketals or cyclic acetals obtained becomes undesirably high.

Examples of ketones in which both $R^1$ and $R^2$ are alkyl groups include acetone, methyl ethyl ketone, methyl propyl ketone, diethyl ketone, methyl isopropyl ketone, methyl butyl ketone, ethyl propyl ketone, methyl sec-butyl ketone, methyl isobutyl ketone, ethyl isopropyl ketone, methyl tert-butyl ketone, methyl amyl ketone, ethyl butyl ketone, diisopropyl ketone, methyl isoamyl ketone, dipropyl ketone, isopropyl propyl ketone, methyl neopentyl ketone, ethyl tert-butyl ketone, methyl hexyl ketone, ethyl pentyl ketone, 6-methyl-2-heptanone, 4-methyl-3-heptanone, 2-methyl-3-heptanone, 5-methyl-3-heptanone, methyl cyclohexyl ketone, methyl heptyl ketone, ethyl hexyl ketone, dibutyl ketone, diisobutyl ketone, methyl octyl ketone, methyl nonyl ketone, dipentyl ketone, methyl decyl ketone, methyl undecyl ketone, dihexyl ketone, 5-(2', 2', 5'-trimethylcyclohexyl)-2-pentanone, 6,10-dimethyl-2-undecanone, methyl tridecyl ketone, diheptyl ketone, methyl tetradecyl ketone, dioctyl ketone, methyl pentadecyl ketone, diisooctyl ketone, methyl hexadecyl ketone, 6,10,14-trimethyl-2-pentadecanone, dinonyl ketone, methyl heptadecyl ketone, methyl octadecyl ketone, and didecyl ketone.

Examples of ketones in which $R^1$ and $R^2$ together form an alkylene group include cyclopropanone, cyclobutanone, cyclopentanone, cyclohexanone, 2-methylcyclopentanone, 3-methylcyclopentanone, 2-methylcyclohexanone, 3-methylcyclohexanone, 4-methylcyclohexanone, cycloheptanone, 2,4-dimethylcyclohexanone, 2,6-dimethylcyclohexanone, cyclooctanone, 2-ethylcyclohexanone, 3-ethylcyclohexanone, 4-ethylcyclohexanone, 3,3,5-trimethylcyclohexanone, 2-tert-butylcyclohexanone, 4-tert-butylcyclohexanone, 2-isopropyl-4-methylcyclohexanone, cyclodecanone, and cyclododecanone.

Examples of aldehydes in which $R^1$ is a hydrogen atom include acetaldehyde, propionaldehyde, butyraldehyde, isobutyraldehyde, valeraldehyde, isovaleraldehyde, 2-methylbutyraldehyde, caproaldehyde, 2-methylpentanal, 3-methylpentanal, 4-methylpentanal, 2-ethylbutanal, 2,3-dimethylbutanal, 3,3-dimethylbutanal, cyclopentylacetaldehyde, heptanal, 2-methylhexanal, 3-methylhexanal, 4-methylhexanal, 5-methylhexanal, 2-ethylpentanal, cyclohexylacetaldehyde, octanal, 2-methylheptanal, 2-ethylhexanal, 2-propylpentanal, 2,4,4-trimethylpentanal, nonylaldehyde, 3,5,5-trimethylhexanal, decylaldehyde, isodecylaldehyde, 3,7-dimethyloctanal, 2-isopropyl-5-methylhexanal, undecanal, dodecanal, tridecylaldehyde, isotridecylaldehyde, hexadecanal, isooctadecanal, octadecanal, and 2-methyloctadecanal.

When the cyclic ketals or cyclic acetals in the first invention are used in a base oil for a working fluid composition for a refrigerating machine, ketones or aldehydes represented by the general formula (II) are preferred among those represented by the general formula (I).

(II)

Ketones or aldehydes represented by the general formula (II) have 2–25 carbon atoms, preferably 2–17 carbon atoms, more preferably 2–11 carbon atoms. When the number of carbon atoms is more than 25, compatibility with hydrofluorocarbons becomes undesirably poor.

$R^3$ represents a hydrogen atom, or a linear, branched, or cyclic alkyl group having 1–12 carbon atoms; preferably it represents a hydrogen atom, or a linear, branched, or cyclic alkyl group having 1–8 carbon atoms; more preferably it represents a hydrogen atom, or a linear, branched, or cyclic alkyl group having 1–5 carbon atoms. $R^4$ represents a linear, branched, or cyclic alkyl group having 1–12 carbon atoms, preferably a linear, branched, or cyclic alkyl group having 1–8 carbon atoms, more preferably a linear, branched, or cyclic alkyl group having 1–5 carbon atoms. Alternatively, $R^3$ and $R^4$ together represent an alkylene group having 2–13 carbon atoms, preferably an alkylene group having 4–10 carbon atoms, more preferably an alkylene group having 4–5 carton atoms. The total number of carbon atoms of $R^3$ and $R^4$ is 1–13, preferably 1–10, more preferably 1–5.

When the number of carbon atoms of $R^3$ or $R^4$ is more than 12, compatibility of the cyclic ketals or cyclic acetals obtained with hydrofluorocarbons becomes undesirably poor. When the number of carbon atoms of the alkylene group which $R^3$ and $R^4$ together form is more than 13, compatibility of the cyclic ketals or cyclic acetals obtained with hydrofluorocarbons becomes undesirably poor. When the total number of carbon atoms of $R^3$ and $R^4$ is more than 13, compatibility of the cyclic ketals or cyclic acetals obtained with hydrofluorocarbons becomes undesirably poor.

From the viewpoint of compatibility with hydrofluorocarbons, the alkyl group represented by $R^3$ or $R^4$ is preferably branched or cyclic rather than linear, and it is preferred for $R^3$ and $R^4$ together not to form an alkylene group rather than to form an alkylene group.

Ketones used in the first invention and represented by the general formulas (I) or (II) are readily obtained by high temperature decarboxylating dimerization of fatty acids, catalytic oxidation of olefins (Wacker process), oxidation or dehydrogenation of secondary alcohols, and oxidation of cycloalkanes. Ketones obtained by Wacker process can be separated and purified by rectification. Aldehydes used in the first invention and represented by the general formulas (I) or (II) are readily prepared by, for example, dehydrogenation of fatty alcohols, hydroformylation of olefins (oxo method), Rosenmund reduction of fatty acid chlorides, and direct hydrogenation of fatty acids. In the case of the oxo method, both linear and branched aldehydes are produced, but they can be separated and purified by rectification.

Reactive derivatives of carbonyl compounds used in the first invention are ketals and acetals which can readily be obtained by the reaction of a ketone or aldehyde as mentioned above with a lower alcohol having 1–6 carbon atoms in the presence of an acid catalyst. Examples of lower alcohols having 1–6 carbon atoms include methanol, ethanol, propanol, isopropyl alcohol, butanol, isobutyl alcohol, sec-butyl alcohol, tert-butyl alcohol, amyl alcohol, isoamyl alcohol, neopentyl alcohol, 1-methylbutanol, 1,1-dimethylpropanol, 1-ethylpropanol, hexanol, isohexyl alcohol, 2-ethylbutanol, 1-methylamyl alcohol, 1,3-dimethylbutanol, and 1-ethylbutanol.

The cyclic ketals or cyclic acetals used in the first invention can be obtained as described below. The reaction between a polyhydric alcohol and a ketone above is ketalization. This reaction requires an acidic catalyst, such as p-toluenesulfonic acid, methanesulfonic acid, and sulfuric acid in an amount of 0.1 to 10 mole %, preferably 1.0 to 7.0 mole %, and more preferably 1.0 to 5.0 mole % to the amount of the polyhydric alcohol. This reaction may be carried out without solvents, or in an inert solvent such as xylene, toluene, benzene, octane, isooctane, heptane, hexane, cyclohexane, pentane, ligroin, and petroleum ether, or in a mixture of these solvents. The reaction temperature depends upon the boiling point of the ketone used, and the reaction is preferably carried out at a temperature of from 40 to 130° C., preferably from 60 to 100° C., while removing the water formed in the process of the reaction. There are also some cases where the reaction can effectively be carried out under a reduced pressure. When the temperature is lower than the above range, the reaction does not proceed; and when the temperature is higher than the above range, marked coloration and side reactions undesirably occur. Also, the reaction may be carried out in a nitrogen stream, nitrogen atmosphere, or dry air. The reaction time varies with reaction conditions employed, but it is generally preferred to continue the reaction for 5 to 200 hours. After neutralization, the cyclic ketals obtained are subjected to pretreatments, such as filtration and washing, and then can be purified by such means as clay adsorption, crystallization, and distillation.

The reaction between a polyhydric alcohol and above aldehyde is acetalization. This reaction requires an acidic catalyst, such as p-toluenesulfonic acid, methanesulfonic acid, and sulfuric acid, in an amount of 0.01 to 5.0 mole %, preferably 0.1 to 2.0 mole % to the amount of the polyhydric alcohol. This reaction may be carried out without solvents, or in an inert solvent such as xylene, toluene, benzene, octane, isooctane, heptane, hexane, cyclohexane, pentane, butane, ligroin, and petroleum ether, or in a mixture of these solvents. The reaction temperature depends upon the boiling point of the aldehyde used, and the reaction is preferably carried out at a temperature of from 20 to 130° C., preferably from 40 to 100° C., while removing the water formed in the process of the reaction. There are also some cases where the reaction can effectively be carried out under a reduced pressure. When the temperature is lower than the above range, the reaction does not proceed; and when the temperature is higher than the above range, marked coloration and side reactions undesirably occur. Also, the reaction may be carried out in a nitrogen stream, nitrogen atmosphere, or dry air. The reaction time varies with reaction conditions employed, but it is generally preferred to continue the reaction for 1 to 30 hours. After neutralization, the cyclic acetals obtained are subjected to pretreatments, such as filtration and washing, and then can be purified by such means as clay adsorption, crystallization, and distillation.

The reaction between a polyhydric alcohol and a ketal, a reactive derivative of ketone, is transketalization. This reaction requires an acidic catalyst, such as p-toluenesulfonic acid, methanesulfonic acid, and sulfuric acid, in an amount of 0.1 to 10 mole %, preferably 1.0 to 7.0 mole %, and more preferably 1.0 to 5.0 mole % to the amount of the polyhydric alcohol. This reaction may be carried out without solvents or in an inert solvent such as xylene, toluene, benzene, octane, isooctane, heptane, hexane, cyclohexane, pentane, ligroin, and petroleum ether, or in a mixture of these solvents. The reaction temperature depends upon the boiling points of the ketal used and the lower alcohol formed, and the reaction is preferably carried out at a temperature of from 40 to 150° C., preferably from 70 to 130° C., while removing the lower alcohol formed in the process of the reaction. There are also some cases where the reaction can effectively be carried out under a reduced pressure. When the temperature is lower than the above range, the reaction does not proceed; and when the temperature is higher than the above range, marked coloration and side reactions undesirably occur. Also, the reaction may be carried out in a nitrogen stream, nitrogen atmosphere, or dry air. The reaction time varies with reaction conditions employed, but it is generally preferred to continue the reaction for 5 to 200 hours. After neutralization, the cyclic ketals obtained are subjected to pretreatments, such as filtration and washing, and then can be purified by such means as clay adsorption, crystallization, and distillation.

The reaction between a polyhydric alcohol and an acetal, a reactive derivative of aldehyde, is transacetalization. This reaction requires an acidic catalyst, such as p-toluenesulfonic acid, methanesulfonic acid, and sulfuric acid, in an amount of 0.01 to 5.0 mole %, preferably 0.1 to 2.0 mole %. This reaction may be carried out without solvents or in an inert solvent such as xylene, toluene, benzene, octane, isooctane, heptane, hexane, cyclohexane, pentane, butane, ligroin, and petroleum ether, or in a mixture of these solvents. The reaction temperature depends upon the boiling point of the acetal used and the lower alcohol formed, and the reaction is carried out at a temperature of from 20 to 150° C., preferably from 50 to 130° C., while removing the lower alcohol formed in the process of the reaction. There are also some cases where the reaction can effectively be carried out under a reduced pressure. When the temperature is lower than the above range, the reaction does not proceed; and when the temperature is higher than the above range, marked coloration and side reactions undesirably occur. Also, the reaction may be carried out in a nitrogen stream, nitrogen atmosphere, or dry air. The reaction time varies with reaction conditions employed, but it is generally preferred to continue the reaction for 1 to 30 hours. After neutralization, the cyclic acetals obtained are subjected to pretreatments, such as filtration and washing, and then can be purified by such means as clay adsorption, crystallization, and distillation.

The ratio of a polyhydric alcohol to a ketone or a ketal, a reactive derivative of ketone, or to an aldehyde or an acetal, a reactive derivative of aldehyde (hereinafter ketone, ketal, aldehyde, and acetal are simply referred to as a carbonyl compound) is A/2 moles of carbonyl compound to 1 mole of polyhydric alcohol (A means the number of hydroxyl groups of a polyhydric alcohol). It is also effective to carry out the reaction with more than A/2 moles of a carbonyl compound to facilitate the reaction, with removal of the excessive carbonyl compound after the completion of the reaction.

The cyclic ketals or cyclic acetals in the first invention can be obtained by reacting one or more polyhydric alcohols with one or more ketones or ketals, the reactive derivatives of ketones; or with one or more aldehydes or acetals, the reactive derivatives of aldehydes. Also, cyclic ketals and cyclic acetals, which are separately produced, may be mixed before use. For example, the cyclic ketal (viscosity of 63.1 mm$^2$/s at 40° C.) obtained from 1 mole of sorbitol and 3 moles of methyl ethyl ketone may be mixed with the cyclic ketal (viscosity of 7.69 mm$^2$/s at 40° C.) obtained from 1 mole of diglycerol and 2 moles of methyl ethyl ketone to achieve a desired viscosity. Specifically, when 1 mole of the cyclic ketal obtained from 1 mole of sorbitol and 3 moles of methyl ethyl ketone is mixed with 1 mole of the cyclic ketal obtained from 1 mole of diglycerol and 2 moles of methyl ethyl ketone, a lubricating oil with VG 22 can be obtained. The above mixture can also be obtained by the reaction among 1 mole of sorbitol, 1 mole of diglycerol, and 5 moles of methyl ethyl ketone. It is also possible to obtain the cyclic ketals or cyclic acetals in the first invention by the reaction between 1 mole of sorbitol and 2 kinds of ketones or aldehydes, for example, 2 moles of 3,5,5-trimethylhexanal and 1 mole of methyl ethyl ketone.

It is preferable that the number of hydroxyl groups remaining unchanged in the cyclic ketals or cyclic acetals obtained is as small as possible. The average number of such unchanged hydroxyl groups accounts for not more than 20% of the number of hydroxyl groups of the starting polyhydric alcohol, preferably not more than 10%, more preferably not more than 5%, still more preferably not more than 3%.

When more than 20% of hydroxyl groups remain unchanged, viscosity becomes undesirably high and boiling and flashing points become undesirably low. When the cyclic ketals or cyclic acetals are used as a base oil for a working fluid composition for a refrigerating machine, it is particularly preferable that the number of unchanged hydroxyl groups is as small as possible. It is not more than 10%, preferably not more than 5%, more preferably not more than 3%, still more preferably not more than 2%, most preferably not more than 1%. When more than 10% of hydroxyl groups remain unchanged, compatibility with hydrofluorocarbons and insulating property become undesirably poor.

When the cyclic ketals or cyclic acetals in the first invention are used as an insulating oil, or as a base oil for a working fluid composition for a refrigerating machine, polyhydric alcohols without ether bonds are preferable because of high insulating property. Therefore, cyclic ketals or cyclic acetals obtained from hexahydric alcohols such as sorbitol, mannitol, galactitol, iditol, talitol, and allitol, or polyhydric alcohols such as erythritol, are more preferable than cyclic ketals or cyclic acetals obtained from alcohols having one ether bond such as diglycerol and ditrimethylolpropane.

When the cyclic ketals or cyclic acetals in the first invention are used as an insulating oil or a base oil for a working fluid composition for a refrigerating machine, those having 1,3-dioxolan and/or 1,3-dioxane structures are preferred because high insulating property is obtained. Of them, those having 1,3-dioxolan structures are particularly preferred. Therefore, alcohols which have hydroxyl groups at adjacent positions, such as erythritol, diglycerol, sorbitol, mannitol, galactitol, iditol, talitol, and allitol, are preferably used. Also, when hexahydric alcohols, such as sorbitol, mannitol, galactitol, iditol, talitol, and allitol, are used, cyclic ketals or cyclic acetals represented by formulas (IIIa) and (IIIb) are obtained, of which those represented by formula (IIIa) having three 1,3-dioxolan structures are preferred because high insulating property is obtained. When erythritol is used, cyclic ketals or cyclic acetals represented by formulas (IVa) and (IVb) are obtained, of which those represented by formula (IVa) having two 1,3-dioxolan structures are preferred because high insulating property is obtained. Hexahydric alcohols such as sorbitol, mannitol, galactitol, iditol, talitol, and allitol, or erythritol tend to give cyclic ketals represented by formulas (IIIa) and (IVa), when being allowed to react with ketones or ketals, and they tend to give cyclic acetals represented by formulas (IIIb) and (IVb), when being reacted with aldehydes or acetals. Therefore, these alcohols are preferably made to react with ketones or ketals.

When the cyclic ketals or cyclic acetals in the first invention are used as a base oil for a working fluid composition for a refrigerating machine, among cyclic ketals or cyclic acetals obtained from polyhydric alcohols having an even number of hydroxyl groups, cyclic ketals or cyclic acetals obtained from hexahydric alcohols represented by formula (III) and cyclic ketals or cyclic acetals obtained from tetrahydric alcohols, such as erythritol, diglycerol and ditrimethylolpropane, represented by formulas (IV) to (VI), are particularly preferable because various physical properties, such as compatibility with hydrofluorocarbons, insulating property, melting point, and viscosity, are in good balance. Cyclic ketals represented by formulas (VIIa) and (VIIb) which are obtained from highly symmetric pentaerythritol are not preferable because they become solid at room temperature, even though the alcohol is tetrahydric. Among the compounds represented by formulas (III) to (VI), those represented by formulas (IIIa), (IIIb), (IVa) and (V), which have 1,3-dioxolan structures, are preferable. Among them, compounds represented by formulas (IIIa), (IVa) and (V), which have only 1,3-dioxolan structures, are more preferable. Among them, compounds represented by (IIIa) and (IVa), which have no ether bond in the polyhydric alcohol moiety, are still more preferable.

The melting point of the cyclic ketals or cyclic acetals in the first invention is preferably not more than 10° C., more preferably not more than −10° C., still more preferably not more than −30° C. Though it is not preferable to singly use as a lubricating oil the cyclic ketals or cyclic acetals represented by formulas (VIIa) and (VIIb) of which melting point exceeds 10° C., they can be used in a limited amount by blending them with the other cyclic ketals or cyclic acetals with low melting points in the first invention or other lubricating oils.

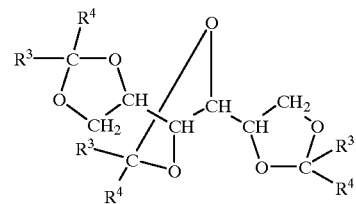

(IIIa)

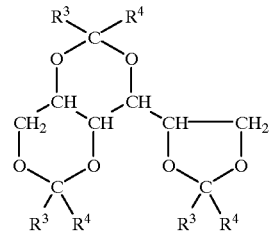

(IIIb)

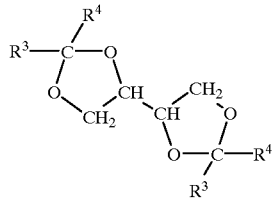

(IVa)

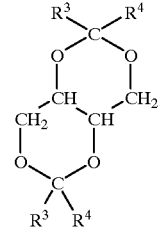

(IVb)

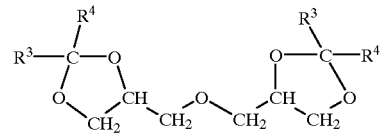

(V)

-continued

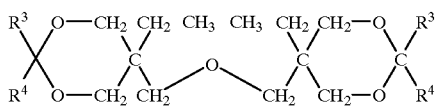

(VI)

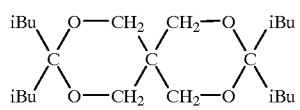

(VIIa)

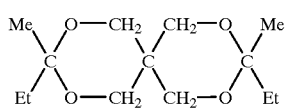

(VIIb)

The cyclic ketals or cyclic acetals used in the first invention preferably have a viscosity at 100° C. of not less than 1 mm²/s and not more than 100 mm²/s, more preferably not less than 1 mm²/s and not more than 50 mm²/s, still more preferably not less than 1 mm²/s and not more than 30 mm²/s.

When the cyclic ketals or cyclic acetals in the first invention are used as a base oil for a working fluid composition for a refrigerating machine, the two-phase separation temperature between the compounds and hydrofluorocarbons is preferably low, being not more than 10° C., preferably not more than 0° C., more preferably not more than –10° C., still more preferably not more than –30° C.

The cyclic ketals or cyclic acetals in the first invention may be blended with other lubricating oils. Such other lubricating oils include mineral oils, hydrocarbon synthetic oils such as polybutenes, poly α-olefins, and alkyl benzenes, aliphatic diesters, neopentyl polyol esters, polyalkylene glycols, poly phenyl ethers, carbonates, phosphate esters, silicate esters, silicone oils, and perfluoropolyethers, specific examples of which are set forth in "New Edition of Physicochemistry of Lubrication" (Saiwai Shobo), "Basics and Application of Lubricating Oils" (Corona), etc.

The mixing ratio between the cyclic ketals or cyclic acetals in the first invention and other lubricating oils is such that the cyclic ketals or cyclic acetals are contained in the blended lubricating oil in an amount of not less than 0.1% by weight, preferably not less than 1.0% by weight, more preferably not less than 5.0% by weight, still more preferably not less than 10% by weight. When the ratio is less than 0.1% by weight, lubricity improving effect and preventive effect against hydrolysis of esters and carbonates are not sufficiently exerted. When the cyclic ketals or cyclic acetals in the first invention are used as a base oil for a working fluid composition for a refrigerating machine, the other lubricating oils to be added preferably have good compatibility with hydrofluorocarbons, preferable examples of which include neopentyl polyol esters, polyalkylene glycols, and carbonates. However, when the cyclic ketals or cyclic acetals in the first invention have sufficiently good compatibility with hydrofluorocarbons, for example, when they have a two-phase separation temperature of not more than –30° C., preferably not more than –50° C., lubricating oils which are less compatible with hydrofluorocarbons, such as alkylbenzenes and mineral oils, may be blended as long as two-phase separation temperature is below 10° C.

Since the cyclic ketals or cyclic acetals in the first invention are good in both compatibility with hydrofluorocarbons and insulating property, it can be used for a working fluid composition for a refrigerating machine as a mixture with hydrofluorocarbons. Also, it can be used as insulating oils because of good insulating property. Since it has intramolecular ring structures, it can be used as traction oils. Good lubricity and high heat resistivity make them usable for engine and turbine oils, gear oils, hydraulic oils, bearing oils, metal working fluids, compressor oils, grease base oils, and the like. It can also be used as an additive for low sulfur gas oils because of its high lubricity. Since it has many oxygen atoms in the molecule, it can be used as an additive for fuel oils such as octane value booster.

When the cyclic ketals or cyclic acetals in the first invention are used as a base oil for a working fluid composition for a refrigerating machine, the mixing ratio of hydrofluorocarbons with a refrigeration oil containing the cyclic ketals or cyclic acetals used in the present invention, i.e. hydrofluorocarbons/refrigeration oil, is normally 50/1 to 1/20 (weight ratio), preferably 10/1 to 1/5 (weight ratio). When the mixing ratio exceeds 50/1, the viscosity of the mixed solution of hydrofluorocarbons and a refrigeration oil becomes low, thereby making it likely to have undesirably poor lubricity. When the mixing ratio of hydrofluorocarbons/refrigeration oil is lower than 1/20, the refrigeration capability is liable to become undesirably poor.

The hydrofluorocarbons used in the first invention include difluoromethane (HFC32), 1,1-difluoroethane (HFC152a), 1,1,1-trifluoroethane (HFC143a), 1,1,1,2-tetrafluoroethane (HFC134a), 1,1,2,2-tetrafluoroethane (HFC134) and pentafluoroethane (HFC125), with a particular preference given to 1,1,1,2-tetrafluoroethane, difluoromethane, pentafluoroethane, and 1,1,1-trifluoroethane. These hydrofluorocarbons may be used singly or as a mixture of two or more kinds of hydrofluorocarbons.

To the cyclic ketals or cyclic acetals in the first invention, conventional lubricating oil additives, such as antioxidants, extreme pressure additives, oiliness improvers, defoaming agents, detergent dispersants, viscosity index improver, anticorrosive agents, and antiemulsifiers may be added according to necessity. Examples of antioxidants used in the present invention include phenol antioxidants, such as 2,6-di-t-butylphenol, 2,6-di-t-butyl-4-methylphenol, and 4,4'-methylenebis(2,6-di-t-butylphenol); amine-based antioxidants, such as p,p-dioctylphenylamine, monooctyldiphenylamine, phenothiazine, 3,7-dioctylphenothiazine, phenyl-1-naphthylamine, phenyl-2-naphthylamine, alkylphenyl-1-naphthylamine, and alkylphenyl-2-naphthylamine; sulfur-based antioxidants, such as alkyl disulfides, thiodipropionic acid esters, and benzothiazoles; and zinc dialkyl dithiophosphate and zinc diaryl dithiophosphate. The amounts of the above additives are 0.05 to 2.0% by weight of the lubricating oil comprising the cyclic ketals and cyclic acetals in the first invention.

Examples of the usable extreme-pressure additives and oiliness improvers are zinc compounds, such as zinc dialkyl dithiophosphates and zinc diaryl dithiophosphates; sulfur compounds, such as thiodipropionic acid esters, dialkyl sulfides, dibenzyl sulfide, dialkyl polysulfides, alkyl mercaptans, dibenzothiophene, and 2,2'-dithiobis (benzothiazole); phosphorus compounds, such as triaryl phosphates, triaryl phosphites, trialkyl phosphites, and trialkyl phosphates; chlorine compounds, such as chlorinated paraffins; molybdenum compounds, such as molybdenum dithiocarbamate, molybdenum dithiophosphate, and molybdenum disulfide; fluorine compounds, such as perfluoroalkyl polyethers, trifluorochloro ethylene polymers, graphitefluoride; silica compounds, such as fatty acid-modified silicones; and graphites. The amount added is 0.05 to 10% by weight of the lubricating oil containing the cyclic ketals or cyclic acetals in the first invention.

Examples of usable defoaming agents are silicone oils, such as dimethylpolysiloxane; and organosilicates, such as diethyl silicate. The amount added is 0.0005 to 1% by weight of the lubricating oil comprising the cyclic ketals or cyclic acetals in the first invention.

Examples of usable detergent dispersants include sulfonates, phenates, salicylates, phosphonates, polybutenyl succinimides, and polybutenyl succinic acid esters. The amount added is 0.05 to 10% by weight of the lubricating oil comprising the cyclic ketals and cyclic acetals in the first invention.

When the cyclic ketals or cyclic acetals in the first invention are used as a base oil for a working fluid composition for a refrigerating machine, addition of benzotriazole and/or benzotriazole derivatives for protecting metal surface; triaryl phosphates and/or triaryl phosphites for improving lubricity; and radical trapping additives such as phenol compounds for improving thermal stability and metal deactivators with chelating ability are effective.

Triaryl phosphates and triaryl phosphites used in the first invention are those having 18–70 carbon atoms, preferably 18–50 carbon atoms. Specifically, examples include triaryl phosphates such as triphenyl phosphate, tricresyl phosphate, trixylenyl phosphate, cresyldiphenyl phosphate, xylenyldiphenyl phosphate, tris(tribromophenyl) phosphate, tris(dibromophenyl) phosphate, tris(2,4-di-tert-butylphenyl) phosphate and trinonylphenyl phosphate; and triaryl phosphites such as triphenyl phosphite, tricresyl phosphite, trixylenyl phosphite, cresyldiphenyl phosphite, xylenyldiphenyl phosphite, tris(2,4-di-tert-butylphenyl) phosphite, trinonylphenyl phosphite, tris(tribromophenyl) phosphite and tris(dibromophenyl)phosphite, with preference given to triphenyl phosphate, tricresyl phosphate, trixylenyl phosphate, tris(2,4-di-tert-butylphenyl) phosphate, triphenyl phosphite, tricresyl phosphite, trixylenyl phosphite, and tris(2,4-di-tert-butylphenyl) phosphite. The amount of triaryl phosphates and/or triaryl phosphites added is normally 0.1 to 5.0% by weight, preferably 0.5 to 2.0% by weight of the lubricating oil comprising the cyclic ketals and cyclic acetals in the first invention.

The amount of benzotriazole and/or benzotriazole derivatives in the first invention added is normally 0.001 to 0.1% by weight, preferably 0.003 to 0.03% by weight of the lubricating oil comprising the cyclic ketals or cyclic acetals in the first invention. The benzotriazole and benzotriazole derivatives used in the present invention are preferably those having 6–50 carbon atoms, more preferably 6–30 carbon atoms. Specifically, examples include benzotriazole, 5-methyl-1H-benzotriazole, 1-dioctylaminomethylbenzotriazole, 1-dioctylaminomethyl-5-methylbenzotriazole, 2-(5'-methyl-2'-hydroxyphenyl) benzotriazole, 2-[2'-hydroxy-3',5'-bis(α,α-dimethylbenzyl)phenyl]-2H-benzotirazole, 2-(3',5'-di-tert-butyl-2'-hydroxyphenyl)benzotriazole, 2-(3'-tert-butyl-5'-methyl-2'-hydroxyphenyl)-5-chlorobenzotriazole, 2-(3',5'-di-tert-butyl-2'-hydroxyphenyl)-5-chlorobenzotriazole, 2-(3',5'-di-tert-amyl-2'-hydroxyphenyl)benzotriazole, 2-(5'-tert-butyl-2'-hydroxyphenyl)benzotriazole, 2-(2'-hydroxy-5'-methylphenyl)benzotriazole, 2-(2'-hydroxy-5'-tert-octylphenyl)benzotriazole and 2-[2'-hydroxy-3'-(3",4",5",6"-tetrahydrophthalimide-methyl)-5'-methylphenyl] benzotriazole, with preference being given to benzotriazole and 5-methyl-1H-benzotriazole.

The amount of the metal deactivators usable in the first invention is normally 0.001 to 2.0% by weight, preferably 0.003 to 0.5% by weight of the lubricating oil comprising the cyclic ketals or cyclic acetals in the present invention. The metal deactivators used in the present invention are preferably those with chelating ability and having 5–50 carbon atoms, preferably 5–20 carbon atoms. Specifically, examples include N,N'-disalicylidene-1,2-diaminoethane, N,N'-disalicylidene-1,2-diaminopropane, N-salicylidene-N'-dimethyl-1,2-diaminoethane, N,N'-disalicylidenehydrazine, N,N'-bis(α,5-dimethylsalicylidene)-1,2-diaminoethane, N,N'-bis(α,5-dimethylsalicylidene)-1,3-propanediamine, N,N'-bis(α,5-dimethylsalicylidnene)-1,6-hexanediamine, N,N'-bis(α,5-dimethylsalicylidene)-1,10-decanediamine, N,N'-bis(α,5-dimethylsalicylidene)ethylenetetramine, salicylaldoxime, 2-hydroxy-5-methylacetophenoxime, acetyl acetone, acetoethyl acetate, aceto-2-ethylhexyl acetate, dimethyl malonate, diethyl malonate, 2-ethylhexyl malonate, anthranilic acid, nitrilotriacetic acid, dihydroxyethylglycine, hydroxyethyl ethylenediamine triacetic acid, hydroxyethylimino diacetic acid, ethylenediamine, 3-mercapto-1,2-propanediol, alizarin, quinizarin, and mercaptobenzothiazole, with preference being given to N,N'-disalicylidene-1,2-diaminoethane, N,N'-disalicylidene-1,2-diaminopropane, acetylacetone, acetoacetate, alizarine, and quinizarin.

The amount of the phenol compounds having radical trapping ability added in the first invention is normally 0.05 to 2.0% by weight, preferably 0.05 to 0.5% by weight of the lubricating oil comprising the cyclic ketals or cyclic acetals in the present invention. Phenol compounds usable in the present invention are those having 6–100 carbon atoms, preferably 10–80 carbon atoms. Specifically, examples include 2,6-di-tert-butylphenol, 2,6-di-tert-butyl-4-methylphenol, 4,4'-methylenebis(2,6-di-tert-butylphenol), 4,4'-butylidenebis(3-methyl-6-tert-butylphenol), 2,2'-methylenebis(4-ethyl-6-tert-butylphenol), 2,2'-methylenebis(4-methyl-6-tert-butylphenol), 4,4'-isopropylidenebisphenol, 2,4-dimethyl-6-tert-butylphenol, tetrakis[methylene-3-(3',5'-di-tert-butyl-4'-hydroxyphenyl) propionate]methane, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 2,2'-dihydroxy-3,3'-di(α-methylcyclohexyl)-5,5'-dimethyldiphenylmethane, 2,2'-isobutylidenebis(4,6-dimethylphenol), bis[3,3-bis-(4'-hydroxy-3'-tert-butylphenyl)butyric acid glycol ester, 2,6-bis(2'-hydroxy-3'tert-butyl-5'-methylbenzyl)-4-methylphenol, 1,1'-bis(4-hydroxyphenyl)cyclohexane, 2,5-di-tert-amylhydroquinone, 2,5-di-tert-butylhydroquinone, 1,4-dihydroxyanthraquinone, 3-tert-butyl-4-hydroxyanisole, 2-tert-butyl-4-hydroxyanisole, 2,4-dibenzoyl resorcinol, 4-tert-butylcatechol, 2,6-di-tert-butyl-4-ethylphenol, 2-hydroxy-4-methoxybenzophenone, 2,4-dihydroxybenzophenone, 2,2'-dihydroxy-4-methoxybenzophenone, 2,4,5-trihydroxybenzophenone, α-tocopherol, bis[2-(2-hydroxy-5-methyl-3-tert-butylbenzyl)-4-methyl-6-tert-butylphenyl] terephthalate, triethylene glycol-bis[3-(3-tert-butyl-5-methyl-4-hydroxyphenyl) propionate], 1,6-hexanediol-bis[3-(3,5-di-tert-butyl-4-hydroxyphenyl) propionate], 3,9-bis[2-(3-tert-butyl-4-hydroxy-5-methylphenyl)propionyloxy]-1,1-dimethylethyl]-2,4,8,10-tetraoxaspiro[5.5]undecane, with preference being given to 2,6-di-tert-butylphenol, 2,6-di-tert-butyl-4-methylphenol, 4,4'-methylenebis(2,6-di-tert-butylphenol), 4,4'-butylidenebis(3-methyl-6-tert-butylphenol), 2,2'-methylenebis(4-ethyl-6-tert-butylphenol), 2,2'-methylenebis(4-methyl-6-tert-butylphenol), 4,4'-isopropylidenebisphenol, 2,4-dimethyl-6-tert-butylphenol, tetrakis[methylene-3-(3',5'-di-tert-butyl-4'- hydroxyphenyl)propionate]methane, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 2,6-di-tert-butyl-4-ethylphenol, 2,6-bis(2'-hydroxy-3'-tert-butyl-5'-methylbenzyl)-4-methylphenol, bis[2-(2-hydroxy-5-methyl-3-tert-butylbenzyl)-4-methyl-6-tert-butylphenyl] terephthalate, triethylene glycol bis[3-(3-tert-butyl-5-methyl-4-hydroxyphenyl)propionate], and 1,6-hexanediol bis[3-(3,5-di-tert-butyl-4-hydroxyphenyl)propionate].

Additives stabilizing freon refrigerants, such as organic tin compounds and boron compounds, may be added. The amount added is 0.001 to 10% by weight of the lubricating oil comprising the cyclic ketals or cyclic acetals in the first invention.

Next, the second invention will be described.

Among the cyclic ketals and the cyclic acetals in the first invention, compounds represented by formulas (IIIa) and (IIIb) are novel compounds. The invention concerning the cyclic acetals including these compounds (those represented by the general formula (i) or (ii)) will be described as the second invention. In the second invention, the cyclic ketals and the cyclic acetals in the first invention are together referred to as "cyclic acetals."

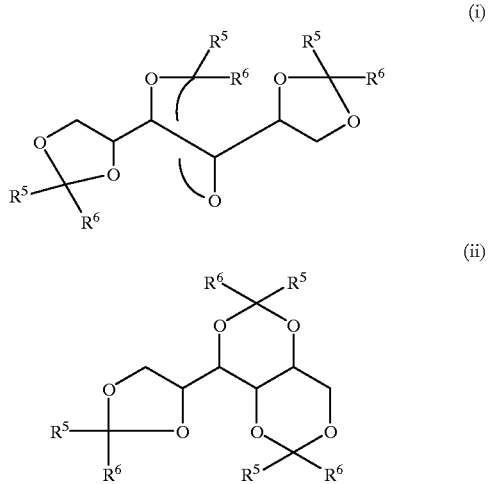

wherein $R^5$ represents a hydrogen atom, and $R^6$ represents a branched alkyl with 3 carbon atoms or a linear or branched alkyl with 4–21 carbon atoms; or $R^5$ represents a linear or branched alkyl with 1–21 carbon atoms, and $R^6$ represents a linear or branched alkyl with 2–21 carbon atoms.

Hexahydric alcohols which give the hexahydric alcohol residue in the compounds represented by the general formula (i) or (ii) include hexitols obtained by reduction of hexoses, such as sorbitol, mannitol, galactitol, iditol, talitol, and allitol.

From the view point of availability and cost, sorbitol is the most preferable.

In the general formula (i) or (ii), when $R^5$ is a hydrogen atom, $R^6$ is a branched alkyl with 3 carbon atoms, or a linear or branched alkyl with 4–21 carbon atoms, preferably a branched saturated alkyl with 3 carbon atoms or a linear or branched saturated alkyl with 4–12 carbon atoms, more preferably a branched saturated alkyl with 3–12 carbon atoms.

The branched alkyl with 3 carbon atoms, represented by $R^6$, is an isopropyl group.

The linear or branched alkyls with 4–21 carbon atoms are exemplified as below.

Specifically, the examples of linear alkyls include butyl, pentyl, hexyl, heptyl, octyl, nonyl, undecyl, tridecyl, pentadecyl, heptadecyl, nonadecyl, and heneicosyl.

Examples of α-methyl-branched alkyls include 1-methylpropyl, 1-methylbutyl, 1-methylpentyl, 1-methylhexyl, 1-methylheptyl, 1-methyloctyl, 1-methylnonyl, 1-methyldecyl, 1-methylundecyl, and 1-methyloctadecyl.

Examples of α-branched alkyls include 1-ethylpropyl, 1-ethylbutyl, 1-ethylpentyl, 1-propylbutyl, 1-ethylhexyl, 1-propylpentyl, 1-ethylheptyl, 1-propylhexyl, 1-butylpentyl, 1-pentylhexyl, 1-hexylheptyl, 1-octylnonyl, 1-hexylundecyl, and 1-decylundecyl.

Examples of α- and other polybranched alkyls having one or more branches at positions other than α-position include 1,2-dimethylpropyl, 1,2-dimethylbutyl, 1,3-dimethylbutyl, 1-ethyl-2-methylpropyl, diisopropylmethyl, 1,4-dimethylpentyl, 1-isopropylbutyl, 1,3,3-trimethylbutyl, 1,5-dimethylhexyl, 1-ethyl-2-methylpentyl, 1-butyl-2-methylpropyl, 1-ethyl-3-methylpentyl, diisobutylmethyl, and 1,5,9-trimethyldecyl.

Examples of β-branched alkyls include 2-methylpropyl, 2-methylbutyl, 2-methylpentyl, 2-ethylbutyl, 2-methylhexyl, 2-ethylpentyl, 2-methylheptyl, 2-ethylhexyl, and 2-propylpentyl.

Examples of β- and other polybranched alkyls having one or more branches at positions other than α- and β-positions include 2,3-dimethylbutyl, 2,4,4-trimethylpentyl, and 2-isopropyl-5-methylhexyl.

Examples of other branched alkyls having one or more branches at positions other than α- and β-positions include 3-methylbutyl, 3-methylpentyl, 4-methylpentyl, 3,3-dimethylbutyl, 3-methylhexyl, 4-methylhexyl, 5-methylhexyl, 3,5,5-trimethylhexyl, isodecyl, 3,7-dimethyloctyl, and isoheptadecyl.

Examples of alkyls having a tertiary carbon with no hydrogen atom at α-position include 1,1-dimethylethyl, 1-methylcyclopropyl, 1,1-dimethylpropyl, 1-methylcyclobutyl, 1,1-dimethylbutyl, 1,1,2-trimethylpropyl, 1-methylcyclopentyl, 1,1-dimethylpentyl, 1-methyl-1-ethylbutyl, 1,1-diethylpropyl, and 1,1-diethylbutyl.

Examples of alkyls having a tertiary carbon with no hydrogen atom at β-position include 2,2-dimethylpropyl, 2,2-dimethylbutyl, 1,2,2-trimethylpropyl, 1-ethyl-2,2-dimethylpropyl, 2,2-dimethylpentyl, and 2,3-dimethyl-2-isopropylbutyl.

Examples of alkyls having a tertiary carbon at both α- and β-positions with no hydrogen atom at both α- and β-positions include 1,1,2,2-tetramethylpropyl, 1,1,2,2-tetramethylbutyl, and 1,1,2,2-tetramethylhexyl.

In formula (i) or (ii), when $R^5$ represents a linear or branched alkyl with 1–21 carbon atoms, $R^6$ represents a linear or branched alkyl with 2–21 carbon atoms. Preferably, $R^5$ is a linear or branched saturated alkyl with 1–12 carbon atoms, and in this case, $R^6$ is preferably a linear or branched saturated alkyl with 2–12 carbon atoms.

In the above-mentioned case, examples of the linear or branched alkyl with 1–21 carbon atoms represented by $R^5$ include methyl, ethyl, propyl and isopropyl in addition to the above-mentioned examples of linear or branched alkyls with 4–21 carbon atoms.

Examples of the linear or branched alkyl with 2–21 carbon atoms represented by $R^6$ include ethyl, propyl and isopropyl in addition to the above-mentioned examples of linear or branched alkyls with 4–21 carbon atoms.

Specific examples (names and structures) of the cyclic acetals represented by the general formula (i) or (ii) as mentioned above are listed below. However, they are not limitative.

(1) 1.2:3.4:5.6-tri-O-(2-methylpropylidene)sorbitol
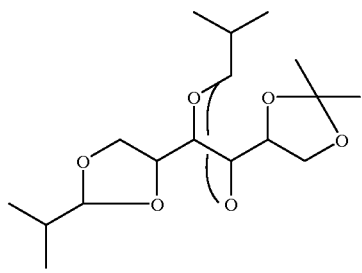
(2) 1.3:2.4:5.6-tri-O-(2-methylpropylidene)sorbitol
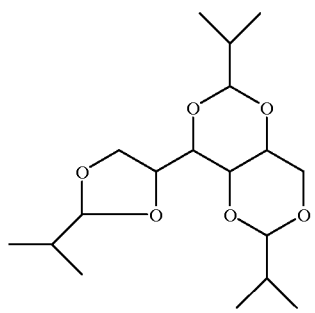
(3) 1.2:3.4:5.6-tri-O-(3,5,5-trimethylhexylidene)sorbitol
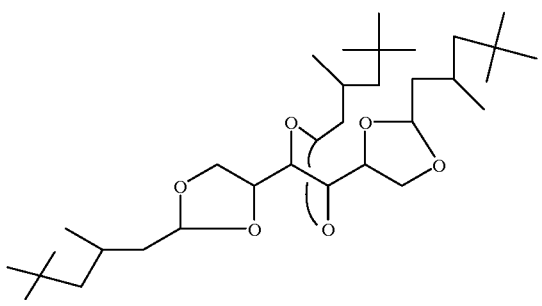
(4) 1.3:2.4:5.6-tri-O-(3,5,5-trimethylhexylidene)sorbitol
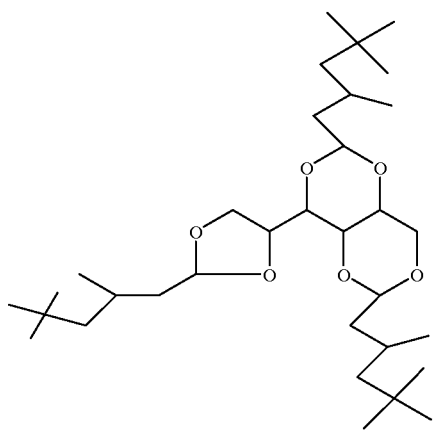
(5) 1.2:3.4:5.6-tri-O-(1-methylpropylidene)sorbitol
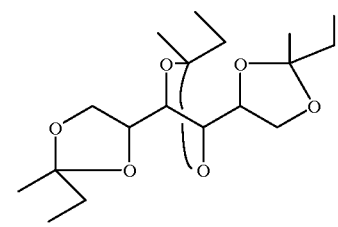
(6) 1.3:2.4:5.6-tri-O-(1-methylpropylidene)sorbitol
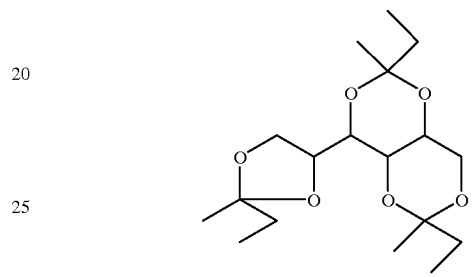
(7) 1.2:3.4:5.6-tri-O-(1,3-dimethylbutylidene)sorbitol
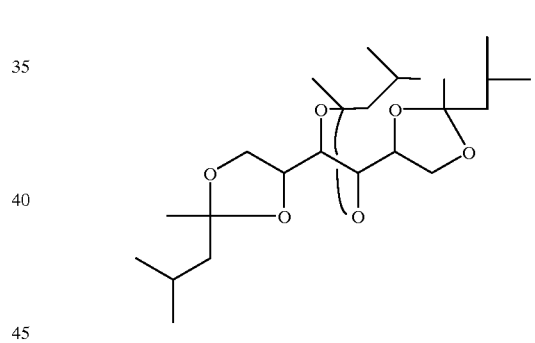
(8) 1.3:2.4:5.6-tri-O-(1,3-dimethylbutylidene)sorbitol
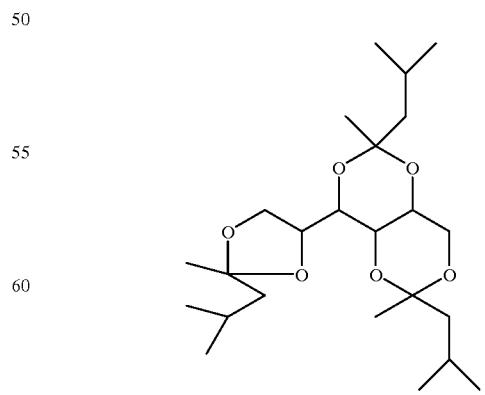

(9) 1.2:3.4:5.6-tri-O-(hexylidene)sorbitol
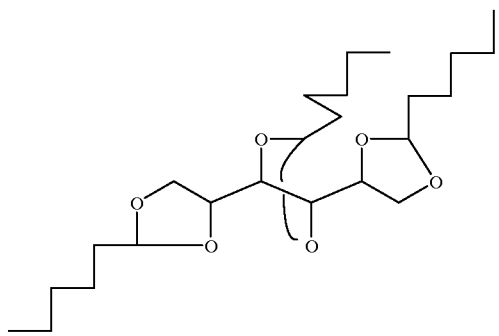
(10) 1.3:2.4:5.6-tri-O-(hexylidene)sorbitol
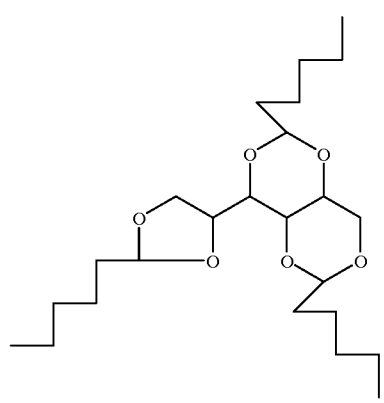
(11) 1.2:3.4:5.6-tri-O-(isooctadecylidene)sorbitol
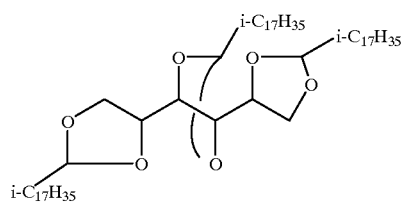
(12) 1.3:2.4:5.6-tri-O-(isooctadecylidene)sorbitol
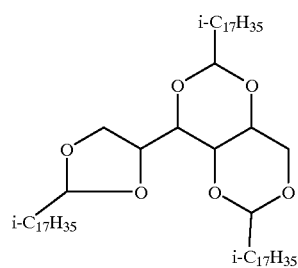
(13) 1.2:3.4:5.6-tri-O-(2-ethylhexylidene)sorbitol
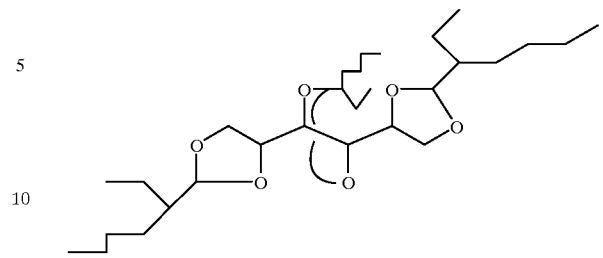
(14) 1.3:2.4:5.6-tri-O-(2-ethylhexylidene)sorbitol
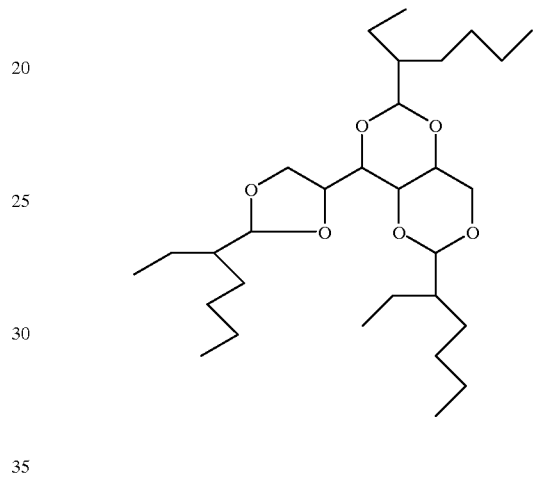
(15) 1.2:3.4:5.6-tri-O-(1-heptadecyloctadecylidene)sorbitol
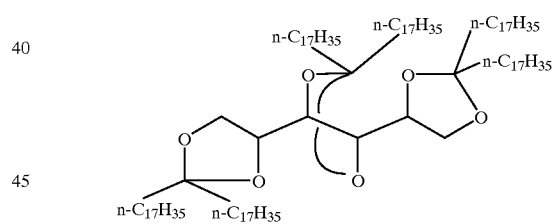
(16) 1.3:2.4:5.6-tri-O-(1-heptadecyloctadecylidene)sorbitol
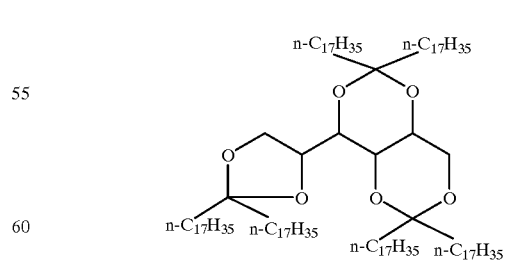

(17) 1.2:3.4:5.6-tri-O-(1-methylpropylidene)mannitol

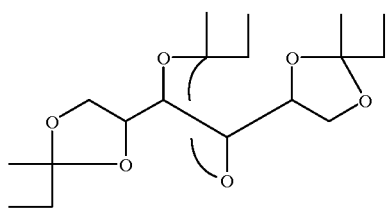

(18) 1.3:2.4:5.6-tri-O-(1-methylpropylidene)mannitol

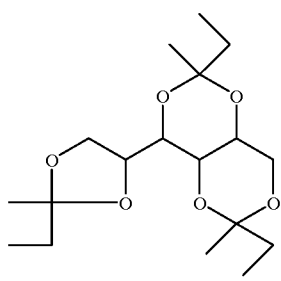

The above cyclic acetals can suitably be produced by the method in the second invention, but it is not limitative.

The cyclic acetals in the second invention are useful as polar oils, organic solvents, lubricants, synthetic lubricating oils, or refrigeration oils, or as intermediates in the production of surfactants, organic solvents, polar oils, synthetic lubricating oils, and refrigeration oils.

Next, the method for producing the cyclic acetals in the second invention will be described.

The method of the present invention is characterized by reacting a hexahydric alcohol with a carbonyl compound (ketone or aldehyde) or with a reactive derivative thereof (ketal or acetal) in the presence of an acid catalyst. The reaction scheme of the relevant reactions is shown below.

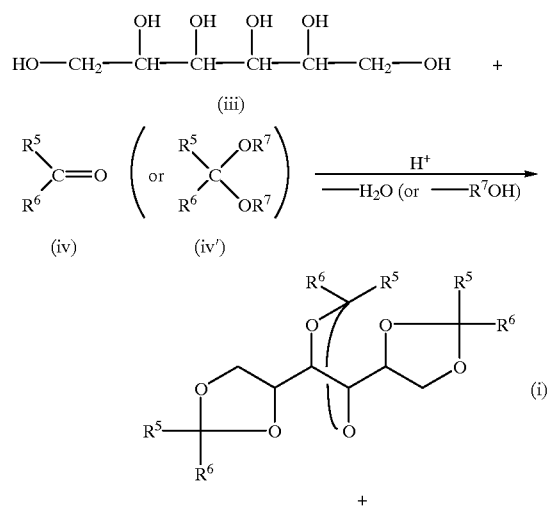

-continued

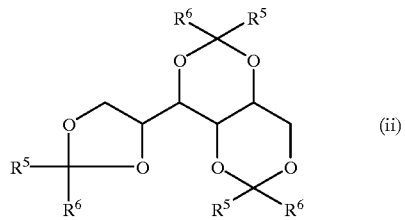

wherein $R^5$ and $R^6$ are defined as the above; and $R^7$ represents a linear or branched alkyl having 1–6 carbon atoms.

In brief, the cyclic acetals represented by the general formula (i) or (ii) are obtained by reacting a hexahydric alcohol such as sorbitol and mannitol represented by the general formula (iii) with a carbonyl compound such as a ketone and an aldehyde represented by the general formula (iv) for dehydration, or with a reactive derivative thereof for dealcoholization, both in the presence of acid catalysts. When a ketone is used, compounds represented by the general formula (i) are predominant, and when an aldehyde is used, compounds represented by the general formulas (i) and (ii) are obtained as a mixture. Aldehydes with an α-branched alkyl group give a higher content of compound (i). Short reaction time leads to a higher content of compound (ii).

The hexahydric alcohols used are those represented by the above formula (iii), whose examples include hexitols obtained by reducing hexoses, such as sorbitol, mannitol, galactitol, iditol, talitol, and allitol. From the viewpoint of availability and cost, sorbitol is the most preferable.

The carbonyl compounds used in the second invention are ketones and aldehydes. Ketones are readily obtained by high temperature decarboxylating dimerization of fatty acids, catalytic oxidation of olefins (Wacker process), oxidation or dehydrogenation of secondary alcohols, and oxidation of cycloalkanes. Ketones obtained by Wacker process show molecular weight distribution, but they can be separated and purified by rectification. Examples of the ketones are as follows, but they are not limitative.

Examples of methyl alkyl ketones include methyl ethyl ketone, methyl propyl ketone, methyl butyl ketone, methyl amyl ketone, methyl hexyl ketone, methyl heptyl ketone, methyl octyl ketone, methyl nonyl ketone, methyl undecyl ketone, and methyl heptadecyl ketone.

Examples of dialkyl ketones include diethyl ketone, ethyl propyl ketone, ethyl butyl ketone, dipropyl ketone, ethyl pentyl ketone, ethyl hexyl ketone, dibutyl ketone, dipentyl ketone, dihexyl ketone, diundecyl ketone, and diheptadecyl ketone.

Examples of polybranched ketones include methyl isopropyl ketone, methyl sec-butyl ketone, methyl isobutyl ketone, ethyl isopropyl ketone, methyl tert-butyl ketone, diisopropyl ketone, methyl isoamyl ketone, isopropyl propyl ketone, methyl neopentyl ketone, ethyl tert-butyl ketone, 6-methyl-2-heptanone, 4-methyl-3-heptanone, 2-methyl-3-heptanone, 5-methyl-3-heptanone, diisobutyl ketone, and 6,10-dimethyl-2-undecanone.

Aldehydes used are those readily prepared by the following methods: dehydrogenation of fatty alcohols, hydroformylation of olefins (oxo method), Rosenmund reduction of fatty acid chlorides, and direct hydrogenation of fatty acids. In the case of the oxo method, both linear and branched aldehydes are produced, but they can be separated and purified by rectification. Examples of the alkyl aldehydes are mentioned below, but they are not limitative.

Examples of linear alkyl aldehydes include valeraldehyde, caproaldehyde, heptanal, octanal, decanal, dodecanal, tetradecanal, octadecanal, and behenaldehyde.

Examples of α-branched alkyl aldehydes include isobutyraldehyde, 2-methylbutyraldehyde, 2-methylpentanal, 2-ethylbutanal, 2-methylhexanal, 2-ethylpentanal, 2-methylheptanal, 2-ethylhexanal, and 2-propylpentanal.

Examples of α- and other polybranched alkyl aldehydes having one or more branches at positions other than α-position include 2,3-dimethylbutanal, 2,4,4-trimethylpentanal, and 2-isopropyl-5-methylhexanal.

Other examples of other branched alkyl aldehydes having one or more branches at positions other than α-position include isovaleraldehyde, 3-methylpentanal, 4-methylpentanal, 3,3-dimethylbutanal, 3-methylhexanal, 4-methylhexanal, 5-methylhexanal, 3,5,5-trimethylhexanal, isodecylaldehyde, 3,7-dimethyloctanal, and isooctadecanal.

Reactive derivatives of carbonyl compounds used in the second invention are ketals and acetals represented by formula (iv') which can readily be synthesized from a ketone or an aldehyde mentioned above and a lower alcohol having 1–6 carbon atoms in the presence of an acid catalyst. Examples of lower alcohols having 1–6 carbon atoms which give $R^7$ residue include methanol, ethanol, propanol, isopropanol, butanol, isobutyl alcohol, sec-butyl alcohol, tert-butyl alcohol, amyl alcohol, isoamyl alcohol, neopentyl alcohol, 1-methylbutanol, 1,1-dimethylpropanol, 1-ethylpropanol, hexanol, isohexyl alcohol, 2-ethylbutanol, 1-methyl-amyl alcohol, 1,3-dimethylbutanol, and 1-ethylbutanol.

In the second invention, the reaction between a hexahydric alcohol represented by formula (iii) and a ketone is ketalization. The molar ratio of the ketone to the hexahydric alcohol represented by formula (iii) is in the range of from 1.5 to 15, preferably from 2.7 to 7.5. This reaction is carried out in the presence of an acidic catalyst, such as p-toluenesulfonic acid, methanesulfonic acid, and sulfuric acid in an amount of 0.1 to 10 mole %, preferably 1.0 to 5 mole % to the amount of the hexahydric alcohol represented by formula (iii).

The above reaction may be carried out without any solvents or in an inert solvent, such as xylene, toluene, benzene, octane, isooctane, heptane, hexane, cyclohexane, pentane, ligroin, and petroleum ether or in a mixture thereof. The reaction temperature depends upon the boiling point of the ketone used, and the reaction is carried out at a temperature of from 30 to 130° C., preferably from 60 to 100° C., while removing the water formed during the reaction. In the above temperature range, the reaction can favorably proceed and coloration due to side reactions is less likely to occur. Also, the reaction may be carried out in a nitrogen stream, nitrogen atmosphere, or dry air. The reaction time varies with reaction conditions employed, but it is generally preferred to continue the reaction for 5 to 200 hours. After neutralization, obtained cyclic ketals (i) or (ii) are subjected to pretreatments, such as filtration and washing. Then, the ketals can be purified by such means as adsorption, crystallization, and distillation.

The reaction between a hexahydric alcohol represented by formula (iii) and an aldehyde is acetalization. The molar ratio of the aldehyde to the hexahydric alcohol represented by formula (iii) is in the range of from 1.5 to 6, preferably from 2.7 to 3.8. This reaction is carried out in the presence of an acidic catalyst, such as p-toluenesulfonic acid, methanesulfonic acid, and sulfuric acid, in an amount of 0.01 to 5 mole %, preferably 0.1 to 2 mole % to the amount of the hexahydric alcohol represented by formula (iii).

The above reaction may be carried out without solvents or in an inert solvent, such as xylene, toluene, benzene, octane, isooctane, heptane, hexane, cyclohexane, pentane, butane, ligroin, and petroleum ether, or in a mixture thereof. The reaction temperature depends upon the boiling point of the aldehyde used, and the reaction is normally carried out at a temperature of from 20 to 130° C., preferably from 40 to 100° C., while removing the water formed during the reaction. In the above temperature range, the reaction can favorably proceed and coloration due to side reactions is less likely to occur. Also, the reaction may be carried out in a nitrogen stream, nitrogen atmosphere, or dry air. The reaction time varies with reaction conditions employed, but it is generally preferred to continue the reaction for 1 to 30 hours. After neutralization, obtained cyclic acetals (i) or (ii) are subjected to pretreatments, such as filtration and washing. Then, the cyclic acetals can be purified by such means as adsorption, crystallization, and distillation.

The reaction between a hexahydric alcohol represented by formula (iii) and a ketal (iv'), a reactive derivative of ketone, is transketalization. The molar ratio of the ketal (iv') to the hexahydric alcohol represented by formula (iii) is in the range of from 1.5 to 15, preferably from 2.7 to 7.5. This reaction is carried out in the presence of an acidic catalyst, such as p-toluenesulfonic acid, methanesulfonic acid, and sulfuric acid, in an amount of 0.1 to 10 mole %, preferably 1.0 to 5 mole % to the amount of the hexahydric alcohol represented by formula (iii).

The above reaction may be carried out without solvent, or in an inert solvent, such as xylene, toluene, benzene, octane, isooctane, heptane, hexane, cyclohexane, pentane, ligroin, and petroleum ether, or in a mixture thereof. Though the reaction temperature depends upon the boiling points of the ketal (iv') used and the lower alcohol formed, the reaction is carried out at a temperature of from 40 to 150° C., preferably from 70 to 130° C., while removing the lower alcohol formed. In the above temperature range, the reaction can favorably proceed and coloration due to side reactions is less likely to occur. Also, the reaction may be carried out in a nitrogen stream, nitrogen atmosphere, or dry air. The reaction time varies with reaction conditions employed, but it is generally preferred to continue the reaction for 5 to 200 hours. After neutralization, obtained cyclic ketals (i) or (ii) are subjected to pretreatments, such as filtration and washing. Then, the cyclic ketals can be purified by such means as adsorption, crystallization, and distillation.

The reaction between a hexahydric alcohol represented by formula (iii) and an acetal (iv'), a reactive derivative of aldehyde, is transacetalization. The molar ratio of the acetal (iv') to the hexahydric alcohol represented by formula (iii) is in the range of from 1.5 to 6, preferably from 2.7 to 3.8. This reaction is carried out in the presence of an acidic catalyst, such as p-toluenesulfonic acid, methanesulfonic acid, and sulfuric acid, in an amount of 0.01 to 5 mole %, preferably 0.1 to 2 mole % to the amount of the hexahydric alcohol represented by formula (iii).

The above reaction may be carried out without solvents, or in an inert solvent, such as xylene, toluene, benzene, octane, isooctane, heptane, hexane, cyclohexane, pentane, butane, ligroin, and petroleum ether, or in a mixture thereof. The reaction temperature depends upon the boiling points of the acetal (iv') used and the lower alcohol formed, and the reaction is normally carried out at a temperature of from 20 to 150° C., preferably from 50 to 130° C., while removing the lower alcohol formed. In the above temperature range, the reaction can favorably proceed and coloration due to side reactions is less likely to occur. Also, the reaction may be carried out in a nitrogen stream, nitrogen atmosphere, or dry air. The reaction time varies with reaction conditions employed, but it is generally preferred to continue the reaction for 1 to 30 hours. After neutralization, obtained cyclic acetals (i) or (ii) are subjected to pretreatments, such as filtration and washing, and then can be purified by such means as adsorption, crystallization, and distillation.

According to the production method in the second invention, when an aldehyde is used, a mixture of formulas (i) and (ii) is obtained, which can be separated by conventional methods for separation and purification of organic compounds, such as rectification, column chromatography, thin layer chromatography, fractional crystallization, preparative HPLC (liquid chromatography), and preparative gas chromatography. However, since physical properties of the both compounds are similar, they can be directly used without separation as a synthetic lubricating oil, a refrigerating oil, and the like.

According to the production method in the second invention, the above-mentioned cyclic acetals can be obtained by a simple method in high yield.

The present invention is hereinafter described in more detail by means of the following production examples, working examples, synthesis examples, and test examples, but is not limited by these examples. Production examples and working examples relate to the first invention, and synthesis examples and test examples relate to the second invention.

PRODUCTION EXAMPLE 1

A 3-liter four-necked flask was equipped with a stirrer, a thermometer, a nitrogen inlet, and a dehydrating column with a condenser. In the flask, 336.8 g (1.85 mol) of D-sorbitol, 800.0 g (11.1 mol) of methyl ethyl ketone, 17.6 g (0.092 mol) of p-toluene sulfonic acid monohydrate, and 200 ml of hexane were placed and heated at a temperature of from 69 to 79° C. in a nitrogen atmosphere for 8 hours with distilling off water. After the completion of the reaction, the reaction mixture was cooled to 60° C., neutralized by adding 19.6 g (0.185 mol, two times the equivalent of p-toluene sulfonic acid) of sodium carbonate, and stirred at 60° C. for 30 minutes. After 200 g of water was added to the mixture and stirred at 60° C. for 30 minutes, the resulting mixture was allowed to stand to separate into two layers. After the lower layer was discarded, the upper layer was washed with 200 g of saturated brine, and evaporated with a rotary evaporator under a reduced pressure to distill away hexane and excessive methyl ethyl ketone. After further reduced-pressure distillation, cyclic ketal $A_1$ was obtained (hydroxyl value of 12.9 mgKOH/g, 97.3% purity as determined by gas chromatography). A part of the cyclic ketal $A_1$ was further purified by column chromatography to give cyclic ketal $A_2$ (hydroxyl value of 0.0 mgKOH/g, 99.8% purity as determined by gas chromatography).

PRODUCTION EXAMPLE 2

A 3-liter four-necked flask was equipped with a stirrer, a thermometer, a calcium chloride tube, and a dehydrating column with a condenser. In the flask, 450.0 g (2.47 mol) of D-sorbitol, 588.0 g (8.15 mol) of isobutyraldehyde, 4.7 g (0.025 mol) of p-toluene sulfonic acid monohydrate, and 400 ml of petroleum ether with a boiling point of 30 to 60° C. were placed and heated at a temperature of from 40 to 65° C. in a dry air atmosphere for 15 hours with distilling off water. After the completion of the reaction, the reaction mixture was cooled to 60° C., neutralized by adding 5.24 g (0.049 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the upper layer was washed with 100 g of saturated brine, and evaporated with a rotary evaporator under a reduced pressure to distill away petroleum ether and excessive isobutyraldehyde. After further reduced-pressure distillation, cyclic acetal B was obtained (hydroxyl value of 6.0 mgKOH/g, 99.0% purity as determined by gas chromatography).

PRODUCTION EXAMPLE 3

A 3-liter four-necked flask was equipped with a stirrer, a thermometer, a calcium chloride tube, and a dehydrating column with a condenser. In the flask, 450.0 g (2.47 mol) of D-sorbitol, 588.0 g (8.15 mol) of n-butyraldehyde, 4.7 g (0.025 mol) of p-toluene sulfonic acid monohydrate, and 400 ml of hexane were placed and heated at a temperature of from 62 to 83° C. in a dry air atmosphere under atmospheric pressure for 5 hours with distilling off water. After the completion of the reaction, the reaction mixture was cooled to 60° C., neutralized by adding 5.24 g (0.049 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of saturated brine, and evaporated with a rotary evaporator under a reduced pressure to distill away hexane and excessive n-butyraldehyde. After further reduced-pressure distillation, cyclic acetal $C_1$ (hydroxyl value of 13.1 mgKOH/g, 97.8% purity as determined by gas chromatography) was obtained. A part of the cyclic acetal $C_1$ was further purified by column chromatography to give cyclic acetal $C_2$ (hydroxyl value of 4.1 mgKOH/g, 99.3% purity as determined by gas chromatography).

PRODUCTION EXAMPLE 4

A 3-liter four-necked flask was equipped with a stirrer, a thermometer, a calcium chloride tube, and a dehydrating column with a condenser. In the flask, 363.8 g (2.00 mol) of D-sorbitol, 1200 g (12.0 mol) of methyl isobutyl ketone, 18.99 g (0.100 mol) of p-toluene sulfonic acid monohydrate, and 300 ml of hexane were placed and heated at a temperature of from 93 to 98° C. in a dry air atmosphere under atmospheric pressure for 23 hours with distilling off water. After the completion of the reaction, the reaction mixture was cooled to 60° C., neutralized by adding 21.16 g (0.200 mol, two times the equivalent of p-toluene sulfonic acid) of sodium carbonate, and stirred at 60° C. for 30 minutes. After 200 g of water was added to the mixture and stirred at 60° C. for 30 minutes, the resulting mixture was allowed to stand to separate into two layers. After the lower layer was discarded, the remaining upper layer was washed with 200 g of saturated brine, and evaporated with a rotary evaporator under a reduced pressure to distill away hexane and excessive methyl isobutyl ketone, and further distill away low-boiling point fractions under a reduced pressure. The 657.6 g of crude ketal thus obtained was filtered through activated clay to give cyclic ketal $D_1$ (hydroxyl value of 34.3 mgKOH/g, 93.1% purity as determined by gas chromatography) was obtained. A part of the cyclic ketal $D_1$ was further purified by column chromatography to give cyclic ketal $D_2$ (hydroxyl value of 0.0 mgKOH/g, 99.6% purity as determined by gas chromatography).

PRODUCTION EXAMPLE 5

A 3-liter four-necked flask was equipped with a stirrer, a thermometer, a calcium chloride tube, and a dehydrating column with a condenser. In the flask, 170.8 g (0.937 mol) of D-sorbitol, 400.0 g (2.81 mol) of 3,5,5-trimethylhexanal, 1.78 g (0.0094 mol) of p-toluene sulfonic acid monohydrate, and 400 ml of hexane were placed and heated at a temperature of from 79 to 81° C. in a dry air under atmospheric pressure for 8 hours with distilling off water. After the completion of the reaction, the reaction mixture was cooled to 70° C., neutralized by adding 1.99 g (0.019 mol, two times the equivalent of p-toluene sulfonic acid) of sodium carbonate, and stirred at 70° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of saturated brine, and evaporated with a rotary evaporator under a reduced pressure to distill away hexane, and further evaporated under a reduced pressure to distill away low-boiling point fractions. To 500.9 g of the crude acetal obtained, 500 ml of hexane was added, and the mixture was filtered through activated clay to give cyclic acetal E (hydroxyl value of 27.2 mgKOH/g, 93.2% purity as determined by gas chromatography) was obtained.

PRODUCTION EXAMPLE 6

A 1-liter four-necked flask was equipped with a stirrer, a thermometer, a nitrogen inlet tube, and a dehydrating column with a condenser. In the flask, 166.0 g (1.00 mol) of diglycerol, 288.0 g (4.00 mol) of methyl ethyl ketone, 3.80 g (0.020 mol) of p-toluene sulfonic acid monohydrate, and 100 ml of hexane were placed and heated at a temperature of from 66 to 81° C. in a nitrogen atmosphere under atomospheric pressure for 15 hours with distilling off water. After the completion of the reaction, the reaction mixture was cooled to 60° C., neutralized by adding 4.24 g (0.040 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of water, and evaporated with a rotary evaporator under a reduced pressure to distill away hexane, and excessive methyl ethyl ketone and further evaporated under a reduced pressure to distill away low-boiling point fractions. To 223.0 g of the crude ketal obtained, 0.6 g of activated alumina was added, and stirred at 50° C. for 30 minutes. After filtration, cyclic ketal $F_1$ (hydroxyl value of 15.7 mgKOH/g, 96.7% purity as determined by gas chromatography) was obtained. A part of the cyclic ketal $F_1$ was further purified by column chromatography to obtain cyclic ketal $F_2$ (hydroxyl value of 0.0 mgKOH, 99.7% purity as determined by gas chromatography).

PRODUCTION EXAMPLE 7

A 1-liter four-necked flask was equipped with a stirrer, a thermometer, a nitrogen inlet, and a dehydrating column with a condenser. In the flask, 100.0 g (0.602 mol) of diglycerol, 180.8 g (1.81 mol) of methyl isobutyl ketone, 2.29 g (0.012 mol) of p-toluene sulfonic acid monohydrate, and 300 ml of toluene were placed and heated at a temperature of from 110 to 119° C. in a nitrogen atmosphere under atmospheric pressure for 55 hours with distilling off water. After the completion of the reaction, the reaction mixture was cooled to 60° C., neutralized by adding 2.54 g (0.024 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 50 g of saturated brine, and evaporated with a rotary evaporator under a reduced pressure to distill away toluene and excessive methyl isobutyl ketone, and further distillated under a reduced pressure to give cyclic ketal $G_1$ (hydroxyl value of 26.2 mgKOH/g, 95.1% purity as determined by gas chromatography). A part of the cyclic ketal $G_1$ was further purified by column chromatography to obtain cyclic ketal $G_2$ (hydroxyl value of 1.6 mgKOH/g, 99.5% purity as determined by gas chromatography).

PRODUCTION EXAMPLE 8

A 3-liter four-necked flask was equipped with a stirrer, a thermometer, a calcium chloride tube, and a dehydrating column with a condenser. In the flask, 332.4 g (2.00 mol) of diglycerol, 853.4 g (6.00 mol) of diisobutyl ketone, 7.61 g (0.040 mol) of p-toluene sulfonic acid monohydrate, and 500 ml of hexane were placed and heated at a temperature of from 96 to 97° C. in a dry air atmosphere under atmospheric pressure for 123 hours with distilling off water. After the completion of the reaction, the reaction mixture was cooled to 60° C., neutralized by adding 8.48 g (0.080 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of saturated brine, and evaporated with a rotary evaporator under a reduced pressure to distill away hexane, and further evaporated under a reduced pressure to distill away diisobutyl ketone. To 666.7 g of the crude ketal obtained, 400 ml of hexane was added, and the mixture was filtered through activated clay. The filtrate was evaporated with a rotary evaporator under a reduced pressure to distill away hexane to give cyclic ketal H (hydroxyl value of 4.0 mgKOH/g, 98.0% purity as determined by gas chromatography).

PRODUCTION EXAMPLE 9

A 1-liter four-necked flask was equipped with a stirrer, a thermometer, a nitrogen inlet, and a dehydrating column with a condenser. In the flask, 166.0 g (1.00 mol) of diglycerol, 289.7 g (2.04 mol) of 3,5,5-trimethylhexanal, 1.90 g (0.010 mol) of p-toluene sulfonic acid monohydrate, and 150 ml of hexane were placed and heated at a temperature of from 75 to 92° C. in a nitrogen atmosphere under atmospheric pressure for 8 hours with distilling off water. After the completion of the reaction, the reaction mixture was cooled to 60° C., neutralized by adding 2.12 g (0.020 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of saturated brine, evaporated with a rotary evaporator under a reduced pressure to distill away hexane, and further distillated under a reduced pressure to distill away low-boiling point fractions. To 405.5 g of the crude acetal obtained, 1.2 g of activated alumina was added, and stirred at 50° C. for 30 minutes. After filtration, cyclic acetal $I_1$ (hydroxyl value of 23.1 mgKOH/g, 94.3% purity as determined by gas chromatography) was obtained. A part of the cyclic acetal $I_1$ was further purified by column chromatography to obtain cyclic acetal $I_2$ (hydroxyl value of 2.7 mgKOH/g, 99.1% purity as determined by gas chromatography).

PRODUCTION EXAMPLE 10

A 1-liter four-necked flask was equipped with a stirrer, a thermometer, a nitrogen inlet, and a dehydrating column with a condenser. In the flask, 100.0 g (0.602 mol) of diglycerol, 205.0 g (1.20 mol) of 6-undecanone, 2.29 g (0.012 mol) of p-toluene sulfonic acid monohydrate, and 300 ml of toluene were placed and heated at a temperature of from 122 to 124° C. in a nitrogen atmosphere under atmospheric pressure for 48 hours with distilling off water. After the completion of the reaction, the reaction mixture was cooled to 60° C., neutralized by adding 2.54 g (0.024 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 50 g of saturated brine, evaporated with a rotary evaporator under a reduced pressure to distill away toluene, and further distillated under a reduced pressure to give cyclic ketal $J_1$ (hydroxyl value of 13.2 mgKOH/g, 96.5% purity as determined by gas chromatography). A part of the cyclic ketal $J_1$ was further purified by column chromatography to obtain cyclic ketal $J_2$ (hydroxyl value of 0.9 mgKOH/g, 99.0% purity as determined by gas chromatography).

PRODUCTION EXAMPLE 11

A 1-liter four-necked flask was equipped with a stirrer, a thermometer, a nitrogen inlet, and a dehydrating column with a condenser. In the flask, 122.0 g (1.00 mol) of meso-erythritol, 288.0 g (4.00 mol) of methyl ethyl ketone, 3.80 g (0.020 mol) of p-toluene sulfonic acid monohydrate, and 100 ml of hexane were placed and heated at a temperature of from 63 to 78° C. in a nitrogen atmosphere under atmospheric pressure for 15 hours with distilling off water. After the completion of the reaction, the reaction mixture was cooled to 60° C., neutralized by adding 4.24 g (0.040 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of water, evaporated with a rotary evaporator under a reduced pressure to distill away hexane and excessive methyl ethyl ketone, and further distillated under a reduced pressure to give cyclic ketal K (hydroxyl value of 1.0 mgKOH/g, 99.4% purity as determined by gas chromatography).

PRODUCTION EXAMPLE 12

A 3-liter four-necked flask was equipped with a stirrer, a thermometer, a calcium chloride tube, and a dehydrating column with a condenser. In the flask, 270.0 g (2.21 mol) of meso-erythritol, 629.0 g (4.42 mol) of 3,5,5-trimethylhexanal, 4.21 g (0.022 mol) of p-toluene sulfonic acid monohydrate, and 600 ml of hexane were placed and heated at a temperature of from 76 to 83° C. in a dry air under atmospheric pressure for 7 hours with distilling off water. After the completion of the reaction, the reaction mixture was cooled to 60° C., neutralized by adding 4.68 g (0.044 mol, two times the equivalent of p-toluene sulfonic acid) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of saturated brine, evaporated with a rotary evaporator under a reduced pressure to distill away hexane, and further distillated under a reduced pressure to distill away low-boiling point fractions. To 781.8 g of the crude acetal obtained, 400 ml of hexane was added, and the mixture was filtered through activated clay. The filtrate was evaporated with a rotary evaporator under a reduced pressure to distill away hexane to give cyclic acetal $L_1$ (hydroxyl value of 20.2 mgKOH/g, 95.3% purity as determined by gas chromatography). A part of the cyclic acetal $L_1$ was further purified by column chromatography to obtain cyclic acetal $L_2$ (hydroxyl value of 5.1 mgKOH/g, 98.0% purity as determined by gas chromatography).

PRODUCTION EXAMPLE 13

A 3-liter four-necked flask was equipped with a stirrer, a thermometer, a nitrogen inlet, and a dehydrating column with a condenser. In the flask, 336.8 g (1.85 mol) of D-mannitol, 800.0 g (11.1 mol) of methyl ethyl ketone, 17.6 g (0.092 mol) of p-toluene sulfonic acid monohydrate, and 200 ml of hexane were placed and heated at a temperature of from 68 to 76° C. for 10 hours in a nitrogen atmosphere under atmospheric pressure with distilling off water. After the completion of the reaction, the reaction mixture was cooled to 60° C., neutralized by adding 19.6 g (0.185 mol, two times the equivalent of p-toluene sulfonic acid) of sodium carbonate, and stirred at 60° C. for 30 minutes. After 200 g of water was added to the mixture and stirred at 60° C. for 30 minutes, the resulting mixture was allowed to stand to separate into two layers. After the lower layer was discarded, the remaining upper layer was washed with 200 g of saturated brine, and evaporated with a rotary evaporator under a reduced pressure to distill away hexane and excessive methyl ethyl ketone, further evaporated under a reduced pressure, and purified by column chromatography to give cyclic ketal M (hydroxyl value of 0.2 mgKOH/g, 99.6% purity as determined by gas chromatography).

PRODUCTION EXAMPLE 14

A 3-liter four-necked flask was equipped with a stirrer, a thermometer, and a dehydrating column with a condenser. In the flask, 500 g (3.73 mol) of trimethylolpropane, 777 g (7.46 mol) of 2,2-dimethoxy propane, 14.17 g (0.075 mol) of p-toluene sulfonic acid monohydrate were placed and heated at a temperature of from 60 to 70° C. for 2 hours in a nitrogen atmosphere under atmospheric pressure with distilling off methanol. After the completion of the reaction, the reaction mixture was subjected to the same post-treatments as in Production Example 13 and then to a reduced-pressure distillation to give 584.9 g of 1,3-dioxa-5-ethyl-2,2-dimethyl-5-cyclohexylmethanol(Na) (90% yield, hydroxyl value of 322.6 mgKOH/g).

A 2-liter four-necked flask was equipped with a stirrer, a thermometer, a condenser, and a dropping funnel, and purged with nitrogen gas. In the flask, 20.0 g (0.5 mol) of sodium hydride (60% content, oily), 450 ml of 1,2-dimethoxyethane, and 150 ml of dimethylsulfoxide were placed. Under a nitrogen atmosphere, 87.1 g (0.5 mol) of the compound (Na) obtained above was dropped over 15 minutes at room temperature, and stirred for further 1 hour. Then, 77.0 g (0.208 mol) of ethylene glycol di-p-tosylate powder (manufactured by Tokyo Kasei, K.K.) was added over 30 minutes. The mixture was stirred overnight at 70° C. under a nitrogen atmosphere, and 750 ml of water and 500 ml of diethyl ether were added and allowed to separate into 2 layers. The aqueous layer was extracted twice with 300 ml of diethyl ether. The organic layer was combined with the ether extracts, and washed three times with 300 ml of 5% sodium carbonate aqueous solution, and dried over a mixture of anhydrous sodium sulfate and anhydrous sodium carbonate. Then, the solvent was distilled away with a rotary evaporator to give 115.3 g of oily substance. This substance was purified by silica gel column chromatography (hexane/ethyl acetate, developing solvent) to give 51 g of ethylene glycol di-[1,3-dioxa-5-ethyl-2,2-dimethyl-5-cyclohexyl] methyl ether (Nb) (99% purity as determined by column chromatography, hydroxyl value of 0.0 mgKOH/g).

A 1-liter four-necked flask was equipped with a stirrer, a thermometer, and a condenser. In the flask, 50 g (0.13 mol) of the above compound (Nb), 500 ml of ethanol, and 50 ml of 1N hydrochloric acid were placed and heated under reflux at a temperature of from 80 to 100° C. in nitrogen atmosphere for 5 hours. The reaction mixture was cooled to room temperature, and neutralized with 1N sodium hydroxide. The residue obtained by completely distilling off the solvent under a reduced pressure was dissolved in water. After electrodialysis, moisture was removed to give 37.6 g of 2,9-diethyl-2,9-dihydroxymethyl-4,7-dioxadecane-1,10-diol (Nc).

A 300-milliliter four-necked flask was equipped with a stirrer, a thermometer, and a dehydrating column with a condenser. In the flask, 37 g (0.13 mol) of compound (Nc) obtained above, 28.1 g (0.39 mol) of methyl ethyl ketone, 0.49 g (0.0026 mol) of p-toluene sulfonic acid monohydrate, and 50 g of hexane were placed and heated at a temperature of from 60 to 70° C. in a nitrogen atmosphere under atmospheric pressure for 8 hours with distilling off water. After the completion of the reaction, the reaction mixture was subjected to the same post-treatments as in Production Example 13, and the solvent was removed by a rotary evaporator to give 52.3 g of an oily substance. This substance was purified by silica gel column chromatography (hexane/ethyl acetate developing solvent) to give 45 g of ethylene glycol di-[1,3-dioxa-2,5-diethyl-2-methyl-5-cyclohexyl]methyl ether (cyclic ketal N)(98.5% purity as determined by column chromatography, hydroxyl value of 0.0 mgKOH/g).

PRODUCTION EXAMPLE 15

In a 3-liter reaction vessel, 292.1 g (2.18 mol) of trimethylolpropane, 474.0 g (8.17 mol) of acetone, 6.0 g (0.0315 mol) of p-toluene sulfonic acid monohydrate, and 900 ml of hexane were placed and refluxed for 24 hours with removing the formed water off the reaction system. The reaction product was neutralized with aqueous solution of sodium hydroxide, and distilled under a reduced pressure to give 5-hydroxymethyl-5-ethyl-2,2-dimethyl-1,3-dioxane.

Next, 17.4 g (0.1 mol) of the above 5-hydroxymethyl-5-ethyl-2,2-dimethyl-1,3-dioxane, 0.19 g (0.001 mol) of 28% by weight sodium methylate methanol solution, and 5 ml of toluene were placed in a 500-milliliter stainless steel autoclave (equipped with a stirrer, a liquid inlet tube, a gas outlet tube, and a thermometer), and the low-boiling point fractions were distilled away through the gas outlet tube by gradually reducing the pressure from atmospheric pressure to a low pressure (0.4 mmHg) over 1 hour while heating at 110° C. After sealing, 58.0 g (1.0 mol) of propylene oxide was introduced into the autoclave through the liquid inlet tube by applying a pressure over 8 hours. After cooling, 21.2 g (0.11 mol) of 28% by weight sodium methylate methanol solution and 150 ml of toluene were added to the reaction product, and low-boiling point products were distilled away from the gas outlet tube by gradually reducing the pressure from atmospheric pressure to a low pressure (0.4 mmHg) over 2 hours with heating at 110° C.

After cooling, 15.6 g (0.11 mol) of methyl iodide was added and the autoclave was tightly sealed, and heated at 60° C. for 3 hours, and further heated at 90° C. for 5 hours. After cooling, 2.8 g of Kyoward 600 (alkali adsorber, manufactured by Kyowa Chemical Industry K.K.) was added, stirred for 1 hour, and filtered to give oil "fa" used as a comparative product (78% purity as determined by gas chromatography). A part of "fa" was purified by column chromatography to give an oil "f" used as a comparative product (85% purity as determined by gas chromatography).

EXAMPLE 1

Hydroxyl values (JIS K-0070), percentages of unchanged hydroxyls to the number of hydroxyls of a starting polyhydric alcohol, which are calculated from the above hydroxyl value, kinematic viscosities at 40° C. and at 100° C. (JIS K-2283), and pour points (JIS K-2269) were determined for the cyclic ketals and cyclic acetals $A_1$ to N obtained in Production Examples and used in the inventive products. The results are shown in Table 1. Also, kinematic viscosities at 40° C. and at 100° C. (JIS K-2283) and pour points (JIS K-2269) were determined for the oils "a" to "f" used in the comparative products. The results are shown in Table 2.

TABLE 1

| | Cyclic ketals · acetals | | | | | |
|---|---|---|---|---|---|---|
| | Starting alcohols | Starting ketones · aldehydes | Hydroxyl value (mgKOH/g) | Unchanged hydroxyls (%) | Viscosity at 40° C. (mm²/s) | Viscosity at 100° C. (mm²/s) | Pour point (° C.) |
| $A_1$ | Sorbitol | methyl ethyl ketone | 12.9 | 1.3 | 66.9 | 4.62 | −32.5 |
| $A_2$ | Sorbitol | methyl ethyl ketone | 0.0 | 0.0 | 63.1 | 4.54 | −32.5 |
| B | Sorbitol | isobutyraldehyde | 6.0 | 0.61 | 167.8 | 5.81 | −25.0 |
| $C_1$ | Sorbitol | n-butyraldehyde | 13.1 | 1.3 | 68.2 | 5.49 | −37.5 |
| $C_2$ | Sorbitol | n-butyraldehyde | 4.1 | 0.42 | 65.6 | 5.42 | −37.5 |

TABLE 1-continued

Cyclic ketals · acetals

| | Starting alcohols | Starting ketones · aldehydes | Hydroxyl value (mgKOH/g) | Unchanged hydroxyls (%) | Viscosity at 40° C. (mm²/s) | Viscosity at 100° C. (mm²/s) | Pour point (° C.) |
|---|---|---|---|---|---|---|---|
| $D_1$ | Sorbitol | methyl isobutyl ketone | 34.3 | 4.2 | 62.3 | 5.61 | −27.5 |
| $D_2$ | Sorbitol | methyl isobutyl ketone | 0.0 | 0.0 | 53.9 | 5.36 | −27.5 |
| E | Sorbitol | 3,5,5-trimethylhexanal | 27.2 | 4.3 | 394.6 | 15.5 | −20.0> |
| $F_1$ | Diglycerol | methyl ethyl ketone | 15.7 | 1.9 | 7.69 | 1.97 | −45.0> |
| $F_2$ | Diglycerol | methyl ethyl ketone | 0.0 | 0.0 | 6.82 | 1.87 | −45.0> |
| $G_1$ | Diglycerol | methyl isobutyl ketone | 26.2 | 3.8 | 9.08 | 2.35 | −20.0> |
| $G_2$ | Diglycerol | methyl isobutyl ketone | 1.6 | 0.24 | 7.83 | 2.16 | −20.0> |
| H | Diglycerol | diisobutyl ketone | 4.0 | 0.73 | 14.5 | 2.99 | −20.0> |
| $I_1$ | Diglycerol | 3,5,5-trimethylhexanal | 23.1 | 4.2 | 32.4 | 5.05 | −45.0> |
| $I_2$ | Diglycerol | 3,5,5-trimethylhexanal | 2.7 | 0.50 | 29.5 | 4.94 | −45.0> |
| $J_1$ | Diglycerol | 6-undecanone | 13.2 | 2.7 | 32.7 | 5.16 | −20.0> |
| $J_2$ | Diglycerol | 6-undecanone | 0.9 | 0.19 | 31.5 | 4.77 | −20.0> |
| K | Erythritol | methyl ethyl ketone | 1.0 | 0.10 | 3.99 | 1.26 | −32.5 |
| $L_1$ | Erythritol | 3,5,5-trimethylhexanal | 20.2 | 3.2 | 36.6 | 4.96 | −37.5 |
| $L_2$ | Erythritol | 3,5,5-trimethylhexanal | 5.1 | 0.84 | 37.7 | 5.05 | −37.5 |
| M | Mannitol | methyl ethyl ketone | 0.2 | 0.02 | 35.2 | 3.63 | −45.0 |
| N | 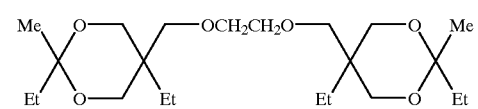 | | 0.0 | 0.0 | 62.8 | 5.29 | −20.0> |

TABLE 2

| Oils used in Comparative Products | | | Viscosity at 40° C. (mm²/s) | Viscosity at 100° C. (mm²/s) | Pour point (° C.) |
|---|---|---|---|---|---|
| a | Naphthene oil (Nippon Sun Oil, Co. Ltd.: SUNISO 4GS) | | 55.5 | 5.87 | −40.0 |
| b | Polyalkylene glycol (Sanyo Kasei Kogyo, Co. Ltd.: Newpol LB-285) | | 60.3 | 11.4 | −40.0 |
| c | Penta- / erythritol | 2-methylhexanoic acid 2-ethylpentanoic acid 2-ethylhexanoic acid esters | 30.9 | 5.21 | −45.0> |
| d | Trimethylol propane | 2-methylhexanoic acid 2-ethylpentanoic acid 3,5,5-trimethylhexanoic acid esters | 31.4 | 5.31 | −45.0> |
| e | Penta- / erythritol | 2-ethylhexanoic acid 3,5,5-trimethylhexanoic acid esters | 62.2 | 7.99 | −45.0> |
| f | 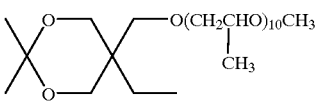 | | 24.5 | 5.5 | −45.0> |

EXAMPLE 2

Compatibility of each of the cyclic ketals and cyclic acetals $A_1$ to $D_2$, $F_1$ to $I_2$, K, M, and N obtained in Production Examples and used in the inventive products with 1,1,1,2-tetrafluoroethane (HFC134a), or with a mixed refrigerant of 1,1,1,2-tetrafluoroethane and difluoromethane (HFC32), or with a mixed refrigerant of 1,1,1,2-tetrafluoroethane, difluoromethane, and pentafluoroethane (HFC125) was evaluated.

Low two-phase separation temperatures were measured for each of the inventive products 1 to 20, each of which was a composition of one of cyclic ketals and cyclic acetals $A_1$ to $D_2$, $F_1$ to $I_2$, K, M, and N with one of 1,1,1,2-tetrafluoroethane (HFC134a), a mixed refrigerant of 1,1,1,2-tetrafluoroethane and difluoromethane (HFC32), and a mixed refrigerant of 1,1,1,2-tetrafluoroethane, difluoromethane and pentafluoroethane (HFC125), and for comparative product 1 which was a composition of oil "a" (nephthene oil) with 1,1,1,2-tetrafluoroethane. The results are shown in Table 3.

As obvious from Table 3, the inventive products exhibit good compatibility with hydrofluorocarbons at low temperatures. Among the inventive products, the compositions containing one of cyclic ketals and cyclic acetals $A_1$, $A_2$, B, $D_1$, $D_2$, $F_1$, $F_2$, $G_2$, K, and M are particularly good. As obvious from the comparisons between cyclic ketals $A_1$ and $A_2$ (between inventive products 1 and 2), between $D_1$ and $D_2$ (between inventive products 6 and 7), and between cyclic acetals $I_1$ and $I_2$ (between inventive products 11 and 17), the smaller the number of unchanged hydroxyls is, the better compatibility with hydrofluorocarbons is achieved.

TABLE 3

| | | Composition | Two-phase separation temperature (° C.) Oil content % (by volume) | | | | | | |
|---|---|---|---|---|---|---|---|---|---|
| | | Oils | Hydrofluorocarbon | 1 | 6 | 10 | 20 | 30 | 40 | 50 |
| Inventive Products | 1 | Cyclic ketal $A_1$ | HFC134a | −67 | −55 | −60 | −67 | −66 | −68 | −69 |
| | 2 | Cyclic ketal $A_2$ | HFC134a | | | −70> | −70> | −70> | −70> | −70> |
| | 3 | Cyclic ketal $A_2$ | HFC134a/HFC32 (70/30 weight ratio) | −70> | | −70> | −57 | −53 | −54 | −57 |
| | 4 | Cyclic acetal B | HFC134a | −70> | | −62 | −44 | −39 | −39 | −42 |
| | 5 | Cyclic acetal $C_1$ | HFC134a | | | 9 | 13 | 14 | 15 | 15 |
| | 6 | Cyclic ketal $D_1$ | HFC134a | | | −4 | 2 | 6 | 5.5 | 5 |
| | 7 | Cyclic ketal $D_2$ | HFC134a | | | −17 | −1 | 5 | 4.5 | 2 |
| | 8 | Cyclic ketal $F_1$ | HFC134a | −70> | −70> | −70> | −70> | −70> | −70> | −70> |
| | 9 | Cyclic ketal $F_1$ | HFC134a/HFC32 (70/30 weight ratio) | | | −70> | −70> | −70> | −70> | −70> |
| | 10 | Cyclic ketal H | HFC134a | | | −10 | 13 | 16 | 13 | 4 |
| | 11 | Cyclic acetal $I_1$ | HFC134a | | | −13 | 10 | 14 | 11 | −2 |
| Comparative Product 1 | | a (naphthene oil) | HFC134a | 20< | | 20< | 20< | 20< | 20< | 20< |
| Inventive Products | 12 | Cyclic ketal $A_2$ | HFC134a/HFC32/HFC125 (52/23/25 weight ratio) | −70> | −70> | −70> | −70> | −70> | −70> | −70> |
| | 13 | Cyclic ketal $F_2$ | HFC134a | −70> | −70> | −70> | −70> | −70> | −70> | −70> |
| | 14 | Cyclic ketal $F_2$ | HFC134a/HFC32 (70/30 weight ratio) | −70> | −70> | −70> | −70> | −70> | −70> | −70> |
| | 15 | Cyclic ketal $F_2$ | HFC134a/HFC32/HFC125 (52/23/25 weight ratio) | −70> | −70> | −70> | −70> | −70> | −70> | −70> |
| | 16 | Cyclic ketal $G_2$ | HFC134a | −70> | −70> | −70> | −70> | −70> | −70> | −70> |
| | 17 | Cyclic ketal $I_2$ | HFC134a | | | −19 | 9 | 12 | 9 | 3 |
| | 18 | Cyclic ketal K | HFC134a | | | −27 | −20 | −17 | −15 | −15 |
| | 19 | Cyclic ketal M | HFC134a | | | −46 | −38 | −30 | −27 | −28 |
| | 20 | Cyclic ketal N | HFC134a | | | −70> | −70> | −70> | −70> | −70> |

EXAMPLE 3

Inventive product 2, a composition comprising cyclic ketal $A_2$ obtained in Production Example and used in the inventive product with 1,1,1,2-tetrafluoroethane (HFC134a), was evaluated for compatibility at high temperatures. In an autoclave with inner volume of 372 cm³ having a sight glass, 60.0 g of cyclic ketal $A_2$ and 240.0 g of HFC134a were weighed, the temperature was increased from room temperature to 100° C. with appropriate stirring, and the state of separation of the mixture was visually checked.

Inventive product 2 (with an oil concentration of 20% by weight) maintained a state of uniform solution from room temperature to 100° C., and showed no phase separation. Similarly, with 20.0 g of cyclic ketal $A_2$ and 380.0 g of HFC 134a, the state of separation was observed. Inventive product 2 (with an oil concentration of 5% by weight) maintained a state of uniform solution from room temperature to 100° C., and showed no phase separation.

Similarly, inventive product 2 with oil concentrations of 10% by weight, 30% by weight, 40% by weight, and 50% by weight maintained a sate of uniform solution from room temperature to 100° C., and did not show phase separation.

EXAMPLE 4

Each of cyclic ketals $A_1$, $A_2$, B, $C_2$, $D_1$, $D_2$, $F_2$, $I_2$, $J_2$, K, $L_2$, M, and N obtained in Production Examples and used in the inventive products, and oils "b" (polyalkylene glycol) and "f" used in the comparative products were evaluated for insulating property. Also, a mixture of cyclic ketal $A_2$ and oil "b" used in the comparative product (weight ratio of 50:50) was similarly tested for insulating property.

According to JIS C-2101, volume resistivity at 25° C. was measured. The results are shown in Table 4.

TABLE 4

| | Oils | Volume resistivity (Ω · cm) |
|---|---|---|
| Oils used in Inventive Products | Cyclic ketal $A_1$ | $1.7 \times 10^{15}$ |
| | Cyclic ketal $A_2$ | $9.4 \times 10^{15}$ |
| | Cyclic ketal $D_1$ | $4.7 \times 10^{14}$ |
| | Cyclic ketal $D_2$ | $5.8 \times 10^{15}$ |
| | Cyclic ketal $A_2$ + Oil "b" used for Comparative product (weight ratio of 50:50) | $1.5 \times 10^{13}$ |
| | Cyclic acetal B | $3.6 \times 10^{14}$ |
| | Cyclic acetal $C_2$ | $1.7 \times 10^{13}$ |
| | Cyclic ketal $F_2$ | $2.1 \times 10^{15}$ |
| | Cyclic acetal $I_2$ | $1.8 \times 10^{14}$ |
| | Cyclic ketal $J_2$ | $1.3 \times 10^{14}$ |
| | Cyclic ketal K | $8.9 \times 10^{15}$ |
| | Cyclic acetal $L_2$ | $7.8 \times 10^{15}$ |
| | Cyclic ketal M | $3.9 \times 10^{15}$ |
| | Cyclic ketal N | $5.4 \times 10^{12}$ |
| Oils used in Comparative Products | b (Polyalkylene glycol) | $7.8 \times 10^{11}$ |
| | f | $8.3 \times 10^{11}$ |

As is obvious from Table 4, the inventive products have high volume resistivities, and better insulating property than the comparative products "b" and "f." Also, the insulating property of polyalkylene glycol can be improved by blending therewith a cyclic ketal or cyclic acetal used in the inventive products. As known from the comparison between cyclic ketals $A_1$ and $A_2$ and between $D_1$ and $D_2$, the less the number of unchanged hydroxyls is, the better insulating property is obtained. Also known from the comparison between cyclic ketal $A_2$ and cyclic acetals B and $C_2$, cyclic ketal $A_2$ obtained from a ketone has a better insulating property than cyclic acetal B or $C_2$ obtained from an aldehyde. NMR analysis and gas chromatography analysis revealed that all cyclic ketal $A_2$ are of IIIa structure, while cyclic acetals B and C are mixtures of IIIa and IIIb structures with ratios (IIIa/IIIb) of 56/44 and 34/66, respectively. Therefore, the more 1,3-dioxolan structure is present, the better insulating property can be achieved. On the other hand, the insulating property of cyclic ketal N having two ether bonds in the moiety of polyhydric alcohol is poorer than that of cyclic ketals or cyclic acetals A to M which have one or no ether bond in the moiety of polyhydric alcohol.

EXAMPLE 5

Each of the inventive products 1, 2, 3, 4, 7, 8, 12, 16, 18, and 19 was subjected to the sealed tube test under the following conditions to examine thermal stability, each inventive product is a composition of one of cyclic ketals or cyclic acetals $A_1$, $A_2$, B, $D_2$, $F_1$, $G_2$, K and M obtained in Production Examples and used in the inventive products with one of 1,1,1,2-tetrafluoroethane (HFC134a), a mixed refrigerant of 1,1,1,2-tetrafluoroethane and difluoromethane, and a mixed refrigerant of 1,1,1,2-tetrafluoroethane, difluoromethane and pentafluoroethane.

Specifically, 10 g of a lubricating oil adjusted to have a water content of not more than 10 ppm and an acid value of not more than 0.03 (mgKOH/g), and 5 g of hydrofluorocarbon were placed in a glass tube; iron, copper, and aluminum were added thereto as catalysts; and the glass tube was sealed. After tested at 175° C. for 14 days, the composition of hydrofluorocarbon and oil was observed for its appearance and presence of precipitation. After the sealed tube was opened to remove hydrofluorocarbon, the acid value of the oil was measured. The results are shown in Table 5.

As is evident from Table 5, all of the inventive products have normal appearance, no precipitation, no increase in acid value, and good thermal stability.

TABLE 5

| | | Physical Properties at the End of Experiment | | |
|---|---|---|---|---|
| | | Appearance | Precipitation | Acid value (mgKOH/g) |
| Inventive Products | 1 | No change | None | 0.03> |
| | 2 | No change | None | 0.03> |
| | 3 | No change | None | 0.03> |
| | 4 | No change | None | 0.03> |
| | 7 | No change | None | 0.03> |
| | 8 | No change | None | 0.03> |
| | 12 | No change | None | 0.03> |
| | 16 | No change | None | 0.03> |
| | 18 | No change | None | 0.03> |
| | 19 | No change | None | 0.03> |

EXAMPLE 6

Each of inventive products 1, 2, 3, 4, 7, 8, 12, 16, 18, and 19 and comparative products 2 and 3 was subjected to the sealed tube test under the following conditions to examine the thermal stability in the presence of water, each inventive product being a composition of one of cyclic ketals and cyclic acetals $A_1$, $A_2$, B, $D_2$, $F_1$, $G_2$, K and M obtained in Production Examples and used in the inventive products with one of 1,1,1,2-tetrafluoroethane (HFC134a), a mixed refrigerant of 1,1,1,2-tetrafluoroethane and difluoromethane, and a mixed refrigerant of 1,1,1,2-tetrafluoroethane, difluoromethane and pentafluoroethane, and each comparative product being a composition of oil "c" or "d" (ester) with 1,1,1,2-tetrafluoroethane (HFC134a). Also, inventive product 21, a composition of a mixture of cyclic ketal $A_1$ and oil "c" used in a comparative product (mixing ratio by weight of 50:50) with 1,1,1,2-tetrafluoroethane (HFC134a), was tested in the similar manner.

Specifically, 10 g of a lubricating oil adjusted to have a water content of 3000 ppm and an acid value of not more than 0.03 (mgKOH/g), and 5 g of hydrofluorocarbon were placed in a glass tube; iron, copper, and aluminum were added thereto as catalysts; and the glass tube was sealed. After tested at 175° C. for 14 days, the composition of oil and hydrofluorocarbon was observed for its appearance and presence or absence of precipitation. After the hydrofluorocarbon was removed, the acid value of the oil was measured. The results are shown in Table 6.

As is evident from Table 6, all of the inventive products have normal appearance, no precipitation, no increase in acid value, and good thermal stability in the presence of water. As shown by inventive product 21, hydrolysis of an ester was prevented by adding cyclic ketals or cyclic acetals in the present invention to the ester.

TABLE 6

| | | Physical Properties at the End of Experiment | | |
|---|---|---|---|---|
| | | Appearance | Precipitation | Acid value (mgKOH/g) |
| Inventive Products | 1 | No change | None | 0.03> |
| | 2 | No change | None | 0.03> |
| | 3 | No change | None | 0.03> |
| | 4 | No change | None | 0.03> |
| | 7 | No change | None | 0.03> |
| | 8 | No change | None | 0.03> |
| | 12 | No change | None | 0.03> |
| | 16 | No change | None | 0.03> |
| | 18 | No change | None | 0.03> |
| | 19 | No change | None | 0.03> |
| | 21 | No change | None | 0.03> |
| Comparative Products | 2 | No change | None | 6.7 |
| | 3 | No change | None | 4.4 |

EXAMPLE 7

Each of inventive products 1 and 4 and comparative products 3 and 4 was subjected to the Falex test to examine anti-abrasion property, each inventive product being a composition of cyclic ketal or cyclic acetal $A_1$ or B obtained in Productive Example and used in the inventive product with 1,1,1,2-tetrafluoroethane (HFC134a), and each comparative products being a composition of oil (ester) "d" or "e" used in the comparative product with 1,1,1,2-tetrafluoroethane (HFC134a).

100 ml of each oil was heated up to 80° C., to which 1,1,1,2-tetrafluoroethane (HFC134a) was blown at 10 L/hour, and the pin was rotated under the load of 150 (lb) for 4 hours, and the abrasion amount in the V block and the pin was determined. The results are shown in Table 7.

As obvious from Table 7, the abrasion amount was very small for all the inventive products, indicating a good anti-abrasion property.

TABLE 7

|  | Abrasion amount (mg) |
| --- | --- |
| Inventive Product 1 | 3.7 |
| Inventive Product 4 | 1.5 |
| Comparative Product 3 | 16.4 |
| Comparative Product 4 | 8.1 |

EXAMPLE 8

Hygroscopicity was evaluated for cyclic ketal $A_2$ obtained in Production Example and used in the inventive product, and for oil "b" (polyalkylene glycol) and oil "c" (ester) used in the comparative products.

Two grams of an oil adjusted in advance to have a water content of not more than 50 ppm was weighed in a glass tube with an inner diameter of 18 mm and a content volume of 10 ml, which was then placed in a vessel at a constant temperature of 25° C. and a humidity of 80%. After a given period of time, the water content of the oil was determined by the Karl Fischer's method (JIS K-2275). The results are shown in Table 8.

As is evident from Table 8, cyclic ketal or cyclic acetal for the inventive product has a significantly low hygroscopicity, which is almost comparable to an ester.

TABLE 8

|  | Water content (ppm) | | | | |
| --- | --- | --- | --- | --- | --- |
|  | Day 0 | Day 1 | Day 3 | Day 6 | Day 9 |
| Oil $A_2$ used in Inventive Product | 45 | 1,965 | 2,575 | 2,588 | 2,697 |
| Oil b used in Comparative Product | 47 | 13,400 | 17,600 | 19,100 | 19,800 |
| Oil c used in Comparative Product | 23 | 1,352 | 1,742 | 1,780 | 1,779 |

EXAMPLE 9

A compressor test was performed with a commercially available rotary compressor with respect to cyclic ketals $A_1$ and $A_2$ obtained in Production Examples and used in the inventive products, and oil "e" (ester) used in the comparative product.

170 g of an oil adjusted in advance to have a water content of not more than 20 ppm and 60 g of 1,1,1,2-tetrafluoroethane (HFC 134a) were weighed in a rotary compressor, and subjected to continuous operation for 500 hours at a compressor shell temperature of 140° C.

After the 500-hour operation, cyclic ketals $A_1$ and $A_2$ have less coloration than the oil "e" for the comparative product, no change in hydroxyl value, no decomposed or polymerized products as analyzed by gas chromatography and gel permeation chromatography, indicating good stability of the oil. Also, as shown in Table 9, cyclic ketals $A_1$ and $A_2$ showed less abrasion of sliding parts as compared with oil "e", indicating a better lubricity. Cyclic ketals $A_1$ and $A_2$ provided a good condition, showing less sludge adhesion to the discharge portion than oil "e" for comparative product.

TABLE 9

|  | Abrasion of blade tip | Adhesion to blade side faces |
| --- | --- | --- |
| Oil $A_1$ used in Inventive Product | 5 μm | None |
| Oil $A_2$ used in Inventive Product | 5 μm | None |
| Oil e used in Comparative Product | 20 μm | Present |

EXAMPLE 10

Lubricity was evaluated by the Falex test for cyclic ketal $A_2$ obtained in Production Example and used in the inventive product.

Cyclic ketal $A_2$ was added to a low sulfur gas oil (S=0.04%) at 50 ppm, the operation was continued for 3 hours at 25° C. under a load of 150 (lb), and abrasion amount in the V block and the pin after the operation was determined. The results are shown in Table 10.

As is evident from Table 10, inventive product 22 to which cyclic ketal $A_2$ was added showed a less amount of abrasion than comparative product 5 to which cyclic ketal $A_2$ was not added. Also, it showed a less amount of abrasion as compared with the gas oil with sulfur content of 0.2% (comparative product 6), exhibiting good lubricity.

TABLE 10

|  |  | Abrasion amount (mg) |
| --- | --- | --- |
| Inventive Product 22 | Low-sulfur gas oil (S = 0.04%) + Cyclic ketal $A_2$ 50 ppm | 20.0 |
| Comparative Product 5 | Low-sulfur gas oil (S = 0.04%) | 38.0 |
| Comparative Product 6 | Gas Oil (0.2%) | 24.8 |

EXAMPLE 11

Lubricity was evaluated by the Soda's pendulum test for cyclic ketal $A_2$ obtained in Production Example and used in the inventive product.

Cyclic ketal $A_2$ was added to a low sulfur gas oil (S=0.04%) at 50 ppm, and determined the coefficient of friction at 25° C. The results are shown in Table 11.

As is evident from Table 11, inventive product 22 to which cyclic ketal $A_2$ was added showed a smaller value of coefficient of friction than comparative product 5 to which cyclic ketal $A_2$ was not added. Also, it showed a smaller value of coefficient of friction as compared with the gas oil with sulfur content of 0.2% (comparative product 6), exhibiting good lubricity.

TABLE 11

|  | Coefficient of Friction |
| --- | --- |
| Inventive Product 22 | 0.164 |
| Comparative Product 5 | 0.328 |
| Comparative Product 6 | 0.304 |

EXAMPLE 12

Dielectric constant at 25° C. was measured according to JIS C-2101 to evaluate the insulating property of cyclic ketals $A_2$, $D_2$, $F_2$, $I_2$, K, $L_2$, and M obtained in Production Examples and used in the inventive products, and oil "b" (polyalkylene glycol) used in the comparative product. The results are shown in Table 12.

As is evident from Table 12, all the inventive products have low dielectric constants, showing good insulating property.

Also, cyclic ketals $A_2$, $D_2$, K and M, and cyclic acetal $L_2$, each having no ether bond, have lower dielectric constants than cyclic ketal $F_2$ and cyclic acetal $I_2$, each having one ether bond, indicating better insulating property.

TABLE 12

| | Oils | Relative dielectric constant |
|---|---|---|
| Oils used in Inventive Products | Cyclic ketal $A_2$ | 2.92 |
| | Cyclic ketal $D_2$ | 2.78 |
| | Cyclic ketal $F_2$ | 3.47 |
| | Cyclic acetal $I_2$ | 3.22 |
| | Cyclic ketal K | 2.65 |
| | Cyclic acetal $L_2$ | 2.50 |
| | Cyclic ketal M | 2.89 |
| Oils used in Comparative Product | b (polyalkylene glycol) | 5.31 |

SYNTHESIS EXAMPLE 1

Synthesis of a mixture of 1.2:3.4:5.6-tri-O-(2-methylpropylidene)sorbitol (1) and 1.3:2.4:5.6-tri-O-(2-methylpropylidene)sorbitol (2):

In a 3-liter reaction vessel equipped with a thermometer, a reflux condenser, a Dean and Stark trap, a calcium chloride tube, and a stirrer, 450 g (2.470 mol) of D-sorbitol, 588 g (8.154 mol) of isobutyraldehyde, 4.70 g (0.0247 mol) of p-toluene sulfonic acid monohydrate, and 400 ml of petroleum ether (b.p. 30 to 60° C.) were placed. After the mixture was heated with stirring at a temperature of from 40 to 65° C. for 15 hours while distilling off a theoretical amount of water. After the completion of the reaction, the reaction mixture was cooled to 60° C., neutralized by adding 5.24 g (0.0494 mol) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of saturated brine, and evaporated to give 868.03 g of the crude mixture of Compounds (1) and (2). The obtained product was subjected to a reduced-pressure distillation to give 800.17 g of a mixture of Compounds (1) and (2).

Yield was 94.0%; b.p., 137 to 149° C./0.3 to 0.6 mmHg; purity as determined by gas chromatography, 99.0% (the ratio of Compound (1)/Compound (2), 88/12 (weight ratio)); and hydroxyl value, 6.0 mgKOH/g (theoretical value 0).

Spectrum of the mixture of Compounds (1) and (2)

IR(NEAT, cm$^{-1}$): 2972, 2936, 2884 (C—H stretching), 1476, 1406, 1368 (C—H deformation), 1194, 1106, 1038 (C—O—C stretching), 722 (CH$_2$ rocking)

$^1$H NMR(CDCl$_3$, δppm):
0.58–1.49 (18H, multiplet, —C$\underline{H}_3$)
1.53–2.13 (3H, multiplet, —C$\underline{H}$(CH$_3$)$_2$)
3.32–3.70, 4.50–4.97 (3H, multiplet, (—O—)$_2$C$\underline{H}$—)
3.70–4.50 (8H, multiplet, —C$\underline{H}_2$C$\underline{H}$C$\underline{H}$C$\underline{H}$C$\underline{H}_2$—)

With 1.0 g of the mixture of Compounds (1) and (2), a preparative silica gel thin layer chromatography was performed using a developing solvent of hexane/ethyl acetate= 9/1. The portions at Rf 0.6 to 0.7 as Compound (1) and at Rf 0.5 as Compound (2) were obtained in amounts of 0.63 g and 0.09 g, respectively.

$^{13}$CNMR(CDCl$_3$, δppm) of Compound (1): 107.7–109.1 indicates 5-membered acetal ring structure.

$^{13}$CNMR(CDCl$_3$, δppm) of Compound (2): 107.7–109.1 and 104.9 indicate 5-membered and 6-membered acetal ring structures, respectively (the intensity ratio of the peak at 107.7–109.1 to the peak at 104.9 was 1:2).

SYNTHESIS EXAMPLE 2

Synthesis of a mixture of 1.2:3.4:5.6-tri-O-(3,5,5-trimethylhexylidene)sorbitol (3) and 1.3:2.4:5.6-tri-O-(3,5,5-trimethylhexylidene)sorbitol (4):

In a 3-liter reaction vessel equipped with a thermometer, a reflux condenser, a Dean and Stark trap, a calcium chloride tube, and a stirrer, 170.76 g (0.937 mol) of D-sorbitol, 400 g (2.812 mol) of 3,5,5-trimethylhexanal, 1.78 g (0.00936 mol) of p-toluene sulfonic acid monohydrate, and 400 ml of hexane were placed. After the mixture was heated with stirring at a temperature of from 79 to 81° C. for 8 hours while distilling off a theoretical amount of water. After the completion of the reaction, the reaction mixture was cooled to 70° C., neutralized by adding 1.99 g (0.0188 mol) of sodium carbonate, and stirred at 70° C. for 30 minutes. After 100 g of water was added to the mixture and stirred at 60° C. for 30 minutes, the resulting mixture was allowed to stand to separate into two layers. After the lower layer was discarded, the remaining upper layer was washed with 100 g of saturated brine, and evaporated to give 529.51 g of the crude mixture of Compounds (3) and (4). The obtained product was subjected to a reduced-pressure distillation and a forerun (b.p. 27–85° C./0.5–0.9 mmHg) was discarded. 500.87 g of the residue was dissolved in 500 ml of hexane. The hexane solution was subjected to an adsorption treatment by passing through 25.04 g (5% by weight to the residue) of activated clay on a filter (PTFE, 0.2 µm) under pressure. After washing the clay with hexane, the hexane was completely distilled away from the hexane solution to give 501.14 g of a mixture of Compounds (3) and (4).

Yield was 96.4%; purity as determined by gas chromatography, 93.2% (the ratio of Compound (3)/Compound (4) is 31/69 (weight ratio)); and hydroxyl value, 27.2 mgKOH/g (theoretical value 0).

IR(NEAT, cm$^{-1}$): 2960, 2908, 2876 (C—H stretching), 1476, 1414, 1396, 1368 (C—H deformation), 1132, 1098, 1042 (C—O—C stretching), 714 (CH$_2$ rocking)

$^1$H NMR(CDCl$_3$, δppm):
0.77–1.40 (42H, multiplet, —CH(C$\underline{H}_3$)C$\underline{H}_2$C(C$\underline{H}_3$)$_3$)
1.40–2.49 (9H, multiplet, —C$\underline{H}_2$C$\underline{H}$(CH$_3$)CH$_2$C(CH$_3$)$_3$)
3.38–3.68, 4.48–5.15 (3H, multiplet, (—O—)$_2$C$\underline{H}$—)
3.68–4.42 (8H, multiplet, —C$\underline{H}_2$C$\underline{H}$C$\underline{H}$C$\underline{H}$C$\underline{H}_2$—)

SYNTHESIS EXAMPLE 3

Synthesis of 1.2:3.4:5.6-tri-O-(1-methylpropylidene) sorbitol (5):

In a 3-liter reaction vessel equipped with a thermometer, a reflux condenser, a Dean and Stark trap, a nitrogen inlet tube, and a stirrer, 336.84 g (1.849 mol) of D-sorbitol, 800 g (11.094 mol) of methyl ethyl ketone, 17.58 g (0.092 mol) of p-toluene sulfonic acid monohydrate, and 200 ml of hexane were placed. After the mixture was heated with stirring at a temperature of from 69 to 79° C. for 8 hours while distilling off a theoretical amount of water. After the completion of the reaction, the reaction mixture was cooled to 60° C., neutralized by adding 19.60 g (0.185 mol) of sodium carbonate, and stirred at 60° C. for 30 minutes. After 200 g of water was added to the mixture and stirred at 60°

C. for 30 minutes, the resulting mixture was allowed to stand to separate into two layers. After the lower layer was discarded, the remaining upper layer was washed with 200 g of saturated brine, and evaporated to give 643.75 g of the crude Compound (5). The obtained product was subjected to a reduced-pressure distillation to give 606.71 g of Compound (5).

Yield was 95.3%; b.p., 136–140° C./0.6 mmHg; purity as determined by gas chromatography, 97.3%; and hydroxyl value 12.9 mgKOH/g (theoretical value 0).

SYNTHESIS EXAMPLE 4

Synthesis of 1.2:3.4:5.6-tri-O-(1-methylpropylidene) sorbitol (5):

In a 2-liter reaction vessel equipped with a thermometer, a reflux condenser, a Dean and Stark trap, and a stirrer, 168.4 g (0.93 mol) of D-sorbitol, 400 g (5.6 mol) of methyl ethyl ketone, 8.8 g (0.046 mol) of p-toluene sulfonic acid monohydrate, and 100 g of hexane were placed. Under nitrogen atmosphere, the mixture was heated with stirring at a temperature of from 65 to 72° C. for 7 hours while distilling off a theoretical amount of water. After the completion of the reaction, the reaction mixture was cooled to 60° C., neutralized by adding 9.8 g (0.09 mol) of sodium carbonate, and stirred at 60° C. for 30 minutes. After 100 g of water was added to the mixture and stirred at 60° C. for 30 minutes, the resulting mixture was allowed to stand to separate into two layers. After the lower layer was discarded, the remaining upper layer was washed with saturated brine until it became neutral, dried over anhydrous sodium sulfate, and filtered. Hexane was distilled off from the filtrate to give 293.5 g of crude Compound (5).

Yield of the crude compound was 92.2%; and hydroxyl value, 18.0 mg KOH/g (theoretical value 0).

100 g of the crude compound was dissolved in 100 ml of hexane, and purified by silica gel column chromatography. Fractions eluted with hexane/ethyl acetate=8/2 were collected and evaporated to give 95 g of Compound (5).

Purity as determined by chromatography was 99.7%; and hydroxyl value 0 mgKOH/g (theoretical value 0).

IR(NEAT, cm$^{-1}$): 2980, 2938, 2890 (C—H stretching), 1470, 1380 (C—H deformation), 1242, 1194, 1140, 1080 (C—O—C stretching), 717 (CH$_2$ rocking)

$^1$H NMR(CDCl$_3$, δppm):
0.72–1.10 (9H, multiplet, —CH$_2$CH$_3$)
1.10–1.48 (9H, multiplet, (—O—)$_2$C(CH$_3$)—)
1.48–1.90 (6H, multiplet, —CH$_2$CH$_3$)
3.71–4.31 (8H, multiplet, —CH$_2$CHCHCHCH$_2$—)

SYNTHESIS EXAMPLE 5

Synthesis of 1.2:3.4:5.6-tri-O-(1,3-dimethylbutylidene) sorbitol (7):

In a 3-liter reaction vessel equipped with a thermometer, a reflux condenser, a Dean and Stark trap, a calcium chloride tube, and a stirrer, 363.76 g (1.997 mol) of D-sorbitol, 1200 g (11.981 mol) of methyl isobutyl ketone, 18.99 g (0.0998 mol) of p-toluene sulfonic acid monohydrate, and 300 ml of hexane were placed. The mixture was heated with stirring at a temperature of from 93 to 98° C. for 23 hours while distilling off a theoretical amount of water. After the completion of the reaction, the reaction mixture was cooled to 60° C., neutralized by adding 21.16 g (0.1996 mol) of sodium carbonate, and stirred at 60° C. for 30 minutes. After 200 g of water was added to the mixture and stirred at 60° C. for 30 minutes, the resulting mixture was allowed to stand to separate into two layers. After the lower layer was discarded, the remaining upper layer was washed with 200 g of saturated brine, and evaporated to give 736.65 g of crude Compound (7). The obtained crude Compound (7) was subjected to a reduced-pressure distillation (b.p. 30.5–141° C./2–0.7 mmHg) and a forerun was discarded. 657.62 g of the residue obtained was subjected to an adsorption treatment by passing through 33 g (5% by weight to the residue) of activated clay on a filter (PTFE, 0.2 μm) by a pressure filtration. As a result, 637.44 g of Compound (7) was obtained.

Yield was 74.5%; purity as determined by gas chromatography, 93.1%; and a hydroxyl value, 34.3 mgKOH/g (theoretical value:0).

SYNTHESIS EXAMPLE 6

Synthesis of 1.2:3.4:5.6-tri-O-(1,3-dimethylbutylidene) sorbitol (7):

In a 1-liter reaction vessel equipped with a thermometer, a reflux condenser, a Dean and Stark trap, a nitrogen inlet tube, and a stirrer, 127.5 g (0.7 mol) of D-sorbitol, 420.7 g (4.2 mol) of methyl isobutyl ketone, 6.7 g (0.035 mol) of p-toluene sulfonic acid monohydrate, and 100 g of toluene were placed. Under nitrogen atmosphere, the mixture was heated with stirring and a dehydration reaction was carried out at 92° C. under a reduced pressure for 8 hours. After the completion of the reaction, the reaction mixture was cooled to 60° C., neutralized by adding 10.6 g (0.1 mol) of sodium carbonate, and stirred at 60° C. for 30 minutes. After 60 g of water was added to the mixture and stirred at 60° C. for 30 minutes, the resulting mixture was allowed to stand to separate into two layers. After the lower layer was discarded, the remaining upper layer was washed with saturated brine until it became neutral and evaporated to distill off toluene to give 247.2 g of crude Compound (7).

Yield of the crude compound was 82.4%; and hydroxyl value, 33.2 mg KOH/g (theoretical value 0).

100 g of the crude compound was dissolved in 100 ml of hexane, and purified by silica gel column chromatography. Fractions eluted with hexane/ethyl acetate=8/2 were collected and evaporated to give 90 g of Compound (7).

Purity as determined by chromatography was 99.4%; and hydroxyl value 0 mgKOH/g (theoretical value 0).

IR(NEAT, cm$^{-1}$): 2984, 2956, 2876 (C—H stretching), 1470, 1378 (C—H deformation), 1242, 1186, 1148, 1096 (C—O—C stretching), 718 (CH$_2$ rocking)

$^1$H NMR(CDCl$_3$, δppm):
0.78–1.10 (18H, multiplet, —CH$_2$CH(CH$_3$)$_2$)
1.22–1.47 (9H, multiplet, (—O—)$_2$C(CH$_3$)—)
1.47–1.68 (6H, multiplet, —CH$_2$CH(CH$_3$)$_2$)
1.68–2.03 (3H, multiplet, —CH$_2$CH(CH$_3$)$_2$)
3.71–4.38 (8H, multiplet, —CH$_2$CHCHCHCH$_2$—)

SYNTHESIS EXAMPLE 7

Synthesis of 1.2:3.4:5.6-tri-O-(1-methylpropylidene) mannitol (17):

In a 3-liter reaction vessel equipped with a thermometer, a reflux condenser, a Dean and Stark trap, and a stirrer, 336.84 g (1.849 mol) of D-mannitol, 800.0 g (11.094 mol) of methyl ethyl ketone, 17.58 g (0.092 mol) of p-toluene sulfonic acid monohydrate, and 200 ml of hexane were placed. Under nitrogen atmosphere, the mixture was heated with stirring at a temperature of from 68 to 76° C. for 10 hours while distilling off a theoretical amount of water. After the completion of the reaction, the reaction mixture was cooled to 60° C., neutralized by adding 19.6 g (0.185 mol) of sodium carbonate, and stirred at 60° C. for 30 minutes. After 200 g of water was added to the mixture and stirred at 60° C. for 30 minutes, the resulting mixture was allowed to stand to separate into two layers. After the lower layer was discarded, the remaining upper layer was washed with 200 g of saturated brine, and evaporated to give 639.06 g of crude Compound (17). The obtained crude Compound (17) was subjected to a reduced-pressure distillation to give 605.76 g of partially purified Compound (17) (yield 95.1%).

b.p. 136–140° C./0.3 mmHg; purity as determined by gas chromatography, 94.2%; and hydroxyl value, 12.7 mgKOH/g (theoretical value 0).

Kinematic viscosities at 40° C. and at 100° C. were 37.65 mm$^2$/s and 3.726 mm$^2$/s, respectively.

150 g of the partially purified Compound (17) was dissolved in 150 ml of hexane, and purified by silica gel column chromatography. Fractions eluted with hexane/ethyl acetate=8/2 were collected and evaporated to give 135 g of Compound (17).

Purity as determined by chromatography, 99.6%; and hydroxyl value 0.2 mgKOH/g (theoretical value 0).

IR(NEAT, cm$^{-1}$): 2986, 2944, 2890 (C—H stretching), 1467, 1377 (C—H deformation), 1242, 1191, 1137, 1077 (C—O—C stretching), 708 (CH$_2$ rocking)

$^1$H NMR(CDCl$_3$, δppm):
0.72–1.13 (9H, multiplet, —CH$_2$C$\underline{H}_3$
1.13–1.50 (9H, multiplet, (—O—)$_2$C(C$\underline{H}_3$)—)
1.50–1.90 (6H, multiplet, —C$\underline{H}_2$CH$_3$)
3.88–4.37 (8H, multiplet, —C$\underline{H}_2$C$\underline{H}$C$\underline{H}$C$\underline{H}$C$\underline{H}$C$\underline{H}_2$—)

TEST EXAMPLE 1

Kinematic viscosities at 40° C. and at 100° C. (JIS K-2283), and pour point (JIS K-2269) were measured for the cyclic acetals in the present invention obtained in Synthesis Examples. The results are shown in Table 13.

TABLE 13

| Compounds | Viscosity at 40° C. (mm$^2$/s) | Viscosity at 100° C. (mm$^2$/s) | Pour point (° C.) |
|---|---|---|---|
| Mixture of Inventive Compounds (1) and (2) (Synthesized according to Synthesis Example 1) | 167.8 | 5.81 | −25.0 |
| Mixture of Inventive Compounds (3) and (4) (Synthesized according to Synthesis Example 2) | 394.6 | 15.5 | <−20.0 |
| Inventive Compound (5) (Synthesized according to Synthesis Example 4) | 63.1 | 4.54 | −32.5 |
| Inventive Compound (7) (Synthesized according to Synthesis Example 6) | 53.9 | 5.36 | −27.5 |
| Inventive Compound (17) (Synthesized according to Synthesis Example 7) | 35.2 | 3.63 | −45.0 |
| Comparative Product 1 (naphthene oil: SUNISO 4GS manufactured by Nippon Sun Petroleum K.K.) | 55.5 | 5.87 | −40.0 |
| Comparative Product 2 (polyalkylene glycol: Newpol LB-285 manufactured by Sanyo Kasei Kogyo K.K.) | 60.3 | 11.4 | −40.0 |
| Comparative Product 3 (2-methylhexanoic acid, 2-ethylpentanoic acid, and 3,5,5-trimethylhexanoic acid esters of trimethylolpropane) | 31.4 | 5.31 | <−45.0 |
| Comparative Product 4 (2-ethylhexanoic acid and 3,5,5-trimethylhexanoic acid esters of pentaerythritol) | 62.2 | 7.99 | <−45.0 |

TEST EXAMPLE 2

Compatibility with 1,1,1,2-tetrafluoroethane (HFC134a) was measured for cyclic acetals in the present invention and comparative products. Specifically, the two-phase separation temperature for 1,1,1,2-tetrafluoroethane at low temperatures was measured at oil concentrations of 10 vol %, 20 vol %, 30 vol %, 40 vol %, and 50 vol %. The results are shown in Table 14.

TABLE 14

| | Two-phase separation at low temperatures (° C.) | | | | |
|---|---|---|---|---|---|
| Compounds | 10 Vol % | 20 Vol % | 30 Vol % | 40 Vol % | 50 Vol % |
| Mixture of Inventive Compounds (1) and (2) (Synthesized according to Synthesis Example 1) | −62 | −44 | −39 | −39 | −42 |
| Inventive Compound (5) (Synthesized according to Synthesis Example 4) | <−70 | <−70 | <−70 | <−70 | <−70 |
| Inventive Compound (7) (Synthesized according to Synthesis Example 6) | −17 | −1 | 5 | 4.5 | 2 |
| Inventive Compound (17) (Synthesized according to Synthesis Example 7) | −46 | −38 | −30 | −27 | −28 |
| Comparative Product 1 (naphthene oil: SUNISO 4GS manufactured by Nippon Sun Petroleum K.K.) | >20 | >20 | >20 | >20 | >20 |

As is evident from Table 14, inventive products show better compatibility than comparative products.

TEST EXAMPLE 3

Volume resistivity at 25° C. was measured for cyclic acetals in the present invention obtained in Synthesis Examples and a comparative product (measured according to JIS C-2101). The results are shown in Table 15.

TABLE 15

| Compounds | Volume Resistivity (Ω · cm) |
|---|---|
| Mixture of Inventive Compounds (1) and (2) (Synthesized according to Synthesis Example 1) | $3.6 \times 10^{14}$ |
| Inventive Compound (5) (Synthesized according to Synthesis Example 4) | $9.4 \times 10^{15}$ |
| Inventive Compound (7) (Synthesized according to Synthesis Example 6) | $5.8 \times 10^{15}$ |
| Inventive Compound (17) (Synthesized according to Synthesis Example 7) | $3.9 \times 10^{15}$ |
| Comparative Product 2 (polyalkylene glycol Newpol LB-285 manufactured by Sanyo Kasei Kogyo K.K.) | $7.8 \times 10^{11}$ |

As is evident from Table 15, inventive compounds show better volume resistivity than a comparative product.

TEST EXAMPLE 4

Anti-abrasion effect was evaluated by the Falex test for the composition of cyclic acetals in the present invention obtained in Synthesis Examples with 1,1,1,2-tetrafluoroethane (HFC134a) and the composition of an ester of comparative products with 1,1,1,2-tetrafluoroethane (HFC134a).

100 ml of the oil was heated to 80° C., into which 1,1,1,2-tetrafluoroethane (HFC134a) was blown at 10

L/hour. 4-hour operation was performed under a load of 150 (lb). After the operation, abrasion amount in the V block and the pin was evaluated. The results are shown in Table 16.

As is evident from Table 16, the abrasion amount was small for all the inventive products, showing good anti-abrasion effect.

TABLE 16

| Compounds | Abrasion amount (mg) |
| --- | --- |
| Mixture of Inventive Compounds (1) and (2) (Synthesized according to Synthesis Example 1) | 1.5 |
| Inventive Compound (5) (Synthesized according to Synthesis Example 3) | 3.7 |
| Comparative Product 3 (2-methylhexanoic acid, 2-ethylpentanoic acid, and 3,5,5-trimethylhexanoic acid esters of trimethylolpropane) | 16.4 |
| Comparative Product 4 (2-ethylhexanoic acid and 3,5,5-trimethylhexanoic acid esters of pentaerythritol) | 8.1 |

Industrial Applicability

The present invention provides a synthetic lubricating oil which shows a good thermal stability, a good oxidation resistance, no formation of carboxylic acid due to hydrolysis and a low hygroscopicity and is inexpensive as well. Also, the composition of the above lubricating oil with hydrofluorocarbon can provide a working fluid composition for a refrigerating machine which shows a good insulating property, favorable hygroscopicity, and no formation of carboxylic acid due to hydrolysis and is inexpensive as well. Moreover, according to the present invention, novel cyclic acetals useful as synthetic lubricating oils can be obtained in high yield and at high purity from inexpensive starting materials.

What is claimed is:

1. A synthetic lubricating oil comprising one or more cyclic ketals or cyclic acetals represented by the general formula (IIIa), (IIIb), (IVa), or (IVb):

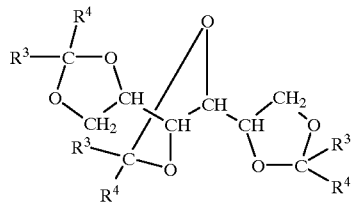
(IIIa)

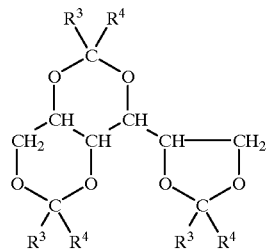
(IIIb)

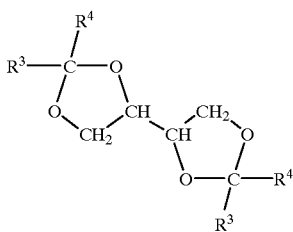
(IVa)

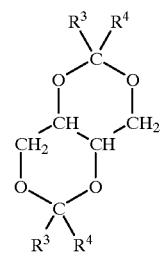
(IVb)

wherein $R^3$ represents a hydrogen atom or a linear, branched, or cyclic alkyl group having 1–12 carbon atoms, $R^4$ represents a linear, branched, or cyclic alkyl group having 1–12 carbon atoms, with the proviso that $R^3$ and $R^4$ are not both methyl, or $R^3$ and $R^4$ together may represent an alkylene group having 2–13 carbon atoms, a total carbon atoms of $R^3$ and $R^4$ being 1–13.

2. A synthetic lubricating oil comprising one or more cyclic ketals or cyclic acetals represented by the general formula (V) or (VI):

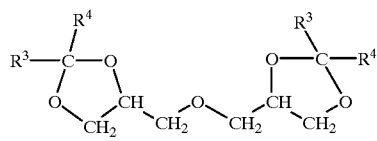
(V)

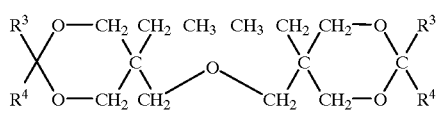
(VI)

wherein $R^3$ represents a hydrogen atom or a linear, branched, or cyclic alkyl group having 1–12 carbon atoms, $R^4$ represents a linear, branched, or cyclic alkyl group having 1–12 carbon atoms, with the proviso that $R^3$ and $R^4$ are not both methyl, or $R^3$ and $R^4$ together may represent an alkylene group having 2–13 carbon atoms, a total carbon atoms of $R^3$ and $R^4$ being 1–13.

3. A working fluid composition for a refrigerating machine comprising a refrigeration oil containing cyclic ketals or cyclic acetals and a hydrofluorocarbon, wherein the hydrofluorocarbon and the refrigerating oil are contained at hydrofluorocarbon/refrigerating oil (weight ratio) of 50/1 to 1/20, wherein said cyclic ketals or cyclic acetals are obtained by a reaction between one or more polyhydric alcohols having an even number of hydroxyl groups of not less than 4 and not more than 8 and one or more of Compound C or D, wherein the Compound C is a carbonyl compound represented by the general formula (II):

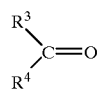
(II)

wherein R³ represents a hydrogen atom or a linear, branched, or cyclic alkyl group having 1–12 carbon atoms; R⁴ represents a linear, branched, or cyclic alkyl group having 1–12 carbon atoms; R³ and R⁴ together may represent an alkylene group having 2–13 carbon atoms, a total carbon atoms of R³ and R⁴ being 1–13, and wherein Compound D is ketals or acetals obtained by a reaction between the carbonyl compound represented by the general formula (II) and a lower alcohol having 1–6 carbon atoms.

4. Cyclic acetals represented by the following general formula (i) or (ii):

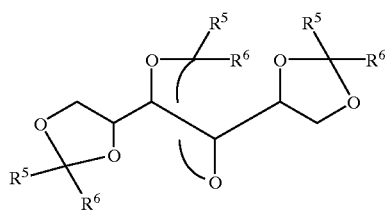
(i)

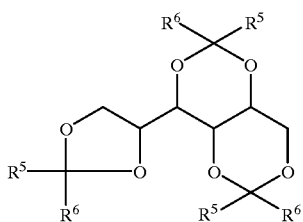
(ii)

wherein
R⁵ represents a hydrogen atom, and R⁶ represents a branched alkyl group having 3 carbon atoms or a linear or branched alkyl group having 4–21 carbon atoms; or R⁵ represents a linear or branched alkyl group having 1–21 carbon atoms, and R⁶ represents a linear or branched alkyl group having 2–21 carbon atoms.

5. The cyclic acetals according to claim 4, wherein R⁵ represents a hydrogen atom, and R⁶ represents a branched alkyl group having 3 carbon atoms or a linear or branched alkyl group having 4–12 carbon atoms; or R⁵ represents a linear or branched alkyl group having 1–12 carbon atoms, and R⁶ represents a linear or branched alkyl group having 2–12 carbon atoms.

6. The cyclic acetals according to claim 4, wherein R⁵ represents a hydrogen atom, and R⁶ represents a branched alkyl group having 3–12 carbon atoms; or R⁵ represents a linear or branched alkyl group having 1–12 carbon atoms, and R⁶ represents a linear or branched alkyl group having 2–12 carbon atoms.

7. The cyclic acetals according to any one of claims 4 to 6, wherein a hexahydric alcohol residue is derived from sorbitol.

* * * * *